(12) United States Patent
Sato et al.

(10) Patent No.: US 6,835,714 B1
(45) Date of Patent: Dec. 28, 2004

(54) HETEROCYCLIC COMPOUNDS, INTERMEDIATES THEREOF AND ELASTASE INHIBITORS

(75) Inventors: Fuminori Sato, Kobe (JP); Yasunao Inoue, Nishinomiya (JP); Tomoki Omodani, Kawanishi (JP); Ryotaro Shiratake, Neyagawa (JP); Seiji Honda, Kobe (JP); Masanobu Komiya, Nagaokakyo (JP); Tadashi Takemura, Mino (JP)

(73) Assignee: Dainippon Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/913,538
(22) PCT Filed: Feb. 23, 2000
(86) PCT No.: PCT/JP00/01022
§ 371 (c)(1), (2), (4) Date: Aug. 15, 2001
(87) PCT Pub. No.: WO00/52032
PCT Pub. Date: Sep. 8, 2000

(30) Foreign Application Priority Data

Mar. 3, 1999 (JP) .......................................... 11/056052

(51) Int. Cl.$^7$ ................................................ C07K 5/06
(52) U.S. Cl. ............................ 514/19; 514/18; 530/331
(58) Field of Search ........................... 530/331; 514/18, 514/19

(56) References Cited

U.S. PATENT DOCUMENTS

| 4,528,133 A | 7/1985 | Kasafirek et al. ........... 530/330 |
| 5,017,610 A | 5/1991 | Imaki et al. ................. 514/546 |

FOREIGN PATENT DOCUMENTS

| EP | 0 189 305 | 7/1986 |
| EP | 0 291 234 | 11/1988 |
| HU | 193048 | 9/1983 |
| WO | 96/31214 | 10/1996 |

OTHER PUBLICATIONS

Chemical Abstracts, vol. 97, No. 7, (1982) Columbus, Ohio, US; Abstract No. 55774p, S. Hashimoto et al., "Formation of 1,4–disubstituted Piperazines by Thermal Degradation of Poly(1–substituted Aziridines). 1", Sci. Eng. Rev. Doshisha Univ., 22 (4), pp. 212–222., Reg. No. 82345–80–0.
S. Takano et al., "Analysis of Cationic and Amphoteric Surfactants: V. Structure Analysis of the Amphoteric Surfactants obtained by the reaction of 1–(2–hydroxyethyl)–2–alkyl–2–imidazoline with sodium monochloroacetate", J. Am. Oil Chem. Soc. (1983), vol. 60, No. 10, pp. 1807–1815, Reg. No. 88245–89–0.
Chemical Abstracts, vol. 114, No. 9, (1991), Columbus, Ohio, US; Abstract No. 81701b, Z. S. Arnold et al., "Hydan-toin–1,3–diacetic acid and its derivative", Pol. J. Chem., 64 (1–6), 1990, pp. 333–338, Reg. No. 132065–89–5.
C. W. Grote et al., "Stereocontrolled Synthesis of DTPA Analogues Branched in the Ethylene Unit", J. Org. Chem., (1995), vol. 60, No. 21, pp. 6987–6997, Reg. No. 171557–30–5.
Chemical Abstracts, vol. 127, No. 293606 (1997), Columbus, Ohio, US; Abstract No. 293606t, A. R. Tapia–Benavides et al., "Syntheses of N–substituted 2,5–piperazinediones", Heterocycles, 45(9), 1997, pp. 1679–1686, Reg. No. 196871–40–6.
M.R. Anelastro et al., "Inhibition of Human Neutrophil Elastase with Peptidyl Electrophilic Ketones. 2. Orally Active PG–Val–Pro–Val Pentafluoroethyl Ketones", J. Med. Chem., (1994), vol. 37, No. 26, pp. 4538–4553.
P.D. Edwards et al., "Discovery and Biological Activity of Orally Active Peptidyl Trifluoromethyl Ketone Inhibitors of Human Neutrophil Elastase", J. Med. Chem., (1997), vol. 40, No. 12, pp. 1876–1885.
Chemical Abstracts, vol. 62, No. 8, (1965) Columbus, Ohio, US; Abstract No. 9129d, G. Kuehn et al., "Ion Exchangers with Complex–Forming Anchor Groups. XII. Existence of Ethylenediaminetriacetic Acid", Z. Chem., 4(12), 1964, pp. 462–463, Reg. No. 730–24–5.
Chemical Abstracts, vol. 63, No. 5, (1966) Columbus, Ohio, US; Abstract No. 6768h, M. Sumoto et al., "Synthesis of some Polyamides and Polyureas Containing the Piperazine Ring", Kogyo Kagaku Zasshi, 68(10), 1989–1994, Reg. No. 7709–77–5.
Chemical Abstracts, vol. 66, No. 15, (1997) Columbus, Ohio, US; Abstract No. 65420u, T.L. Patton et al., "Reactions of Isocyanates with Cyanohydrins. Synthesis of 2,4–oxozolidinediones and 1,3–disubstituted Parabanic Acids", J. Org. Chem., 32(2), 1967, pp. 383–388, Reg. No. 10319–59–2.

*Primary Examiner*—Jon P. Weber
*Assistant Examiner*—David Lukton
(74) *Attorney, Agent, or Firm*—Wenderoth, Lind & Ponack, L.L.P.

(57) ABSTRACT

The present invention relates to a heterocyclic compound of the following formula (I-a), its ester, or a salt thereof, and a human neutrophilic elastase inhibitor containing the same as the active ingredient, etc.

(I-a)

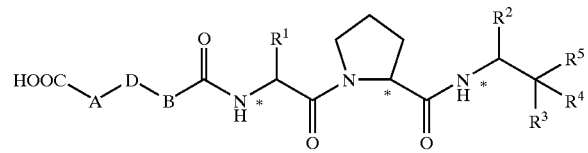

wherein A and B are the same or different and each is a lower alkylene group being optionally substituted by an oxo group, D is a heteromonocyclic or heterobicyclic group being optionally substituted by an oxo group, $R^1$ and $R^2$ are the same or different and each is a lower alkyl group, $R^3$ and $R^4$ are different from each other, and each is a hydrogen atom or a hydroxy group, or both combine together to form an oxo group, and $R^5$ is 2-benzoxazolyl, trifluoromethyl, benzylamino-carbonyl, etc.

9 Claims, No Drawings

HETEROCYCLIC COMPOUNDS, INTERMEDIATES THEREOF AND ELASTASE INHIBITORS

This application is a 371 of PCT/JP00/01022 filed Feb. 23, 2000.

TECHNICAL FIELD

The present invention relates to a novel heterocyclic compound being useful as a medicament, especially exhibiting a human neutrophilic elastase inhibitory activity, intermediates thereof, and a human neutrophilic elastase inhibitor containing as the active ingredient said heterocyclic compound.

PRIOR ART

Human neutrophilic elastase (hereinafter, occasionally simply referred to as elastase) is a kind of serine proteases being massively released from the granules of neutrophile, which appear in the cases of infections or inflammatory diseases. Elastase is an enzyme hydrolyzing proteins such as elastin, collagen, proteoglycan, fibronectin, etc. which constitute the interstitum of intravital connective tissues such as lung, cartilage, vascular wall, skin, etc. In addition, it has been clarified that elastase acts on other proteins or cells as well.

In the living body, elastase keeps the homeostasis of the living body while the activities thereof are controlled by endogenous inhibitor proteins such as $\alpha_1$-protease inhibitor, $\alpha_2$-macrogloblin, secretory leukocyte protease inhibitor, etc. However, when a balance between elastase and the endogenous inhibitors is lost by the excessive release of elastase in the inflammation site or by the lowering in the inhibitor level, the control of elastase activities cannot be kept, by which tissues are injured.

Diseases in which elastase may participate are, for example, pulmonary emphysema, adult respiratory distress syndrome (ARDS), idiopathic interstitial pneumonia (IIP), cystic pulmonary fibrosis, chronic interstitial pneumonia, chronic bronchitis, chronic sinopulmonary infection, diffuse panbronchiolitis, bronchiectasis, asthma, pancreatitis, nephritis, hepatic failure, chronic rheumatoid arthritis, joint scleroma, osteoarthritis, psoriasis, periodontitis, atherosclerosis, rejection against organ transplant, premature amniorrhexis, bullous dermatosis, shock, sepsis, systemic lupus erythematosus (SLE), Crohn's disease, disseminated intracapillary coagulation (DIC), tissue injury after ischemia-reperfusion, formation of cornea cicatricial tissue, myelitis, etc.

Therefore, an elastase inhibitor can be expected to be useful in the prophylaxis or treatment of these diseases. Under these expectations, various elastase inhibitors have been reported.

For example, European Patent Publication No. 189305 (hereinafter, occasionally referred to as Ref. 1) discloses a compound of the following formula (A-1), and it discloses that said compound (A-1) is useful as an elastase inhibitor.

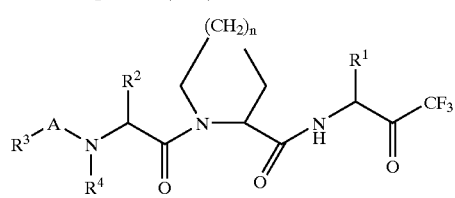

(A-1)

wherein $R^1$ is a lower alkyl having 1 to 5 carbon atoms, $R^2$ is a lower alkyl having 1 to 10 carbon atoms, etc., $R^4$ is a hydrogen atom, etc., A is —CO—, etc., and n is 0, 1 or 2.

Within the above formula, the compound of the following formula is included.

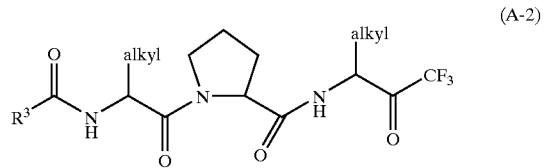

(A-2)

$R^3$ of the above formula (A-2) represents various substituents, but it does not mean the specific substituents included within the present compounds as mentioned below.

In addition, European Patent Publication No. 291234 (hereinafter, occasionally referred to as Ref. 2) discloses a compound of the following formula (B-1), and it also discloses that said compound (B-1) exhibits a leukocyte elastase inhibitory activity.

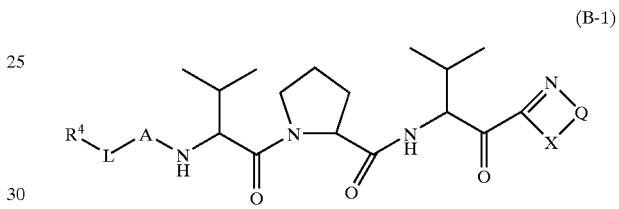

(B-1)

wherein Q is an orthophenylene group optionally having a substituent such as a halogen, etc., X is an oxygen atom or a sulfur atom, A is —CO—, etc., L is a phenylene, a ($C_1$–$C_6$) alkanediyl, etc., and $R^6$ is an acylsulfonamide, etc.

Moreover, the following compound (a) is disclosed in Example 2(63) of U.S. Pat. No. 5,017,610 (hereinafter, occasionally referred to as Ref. 3). The chemical structure of said compound (a) is completely different from the chemical structure of the present compounds. However, said compound (a) should be noted because it has been most developed and studied as a water-soluble elastase inhibitor.

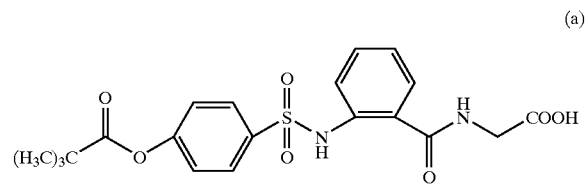

(a)

DISCLUSORE OF INVENTION

An object of the present invention is to provide a novel heterocyclic compound having a potent elastase inhibitory activity and an intermediate thereof.

The present invention relates to a novel heterocyclic compound of the following formula (I-a), its ester, and a salt thereof.

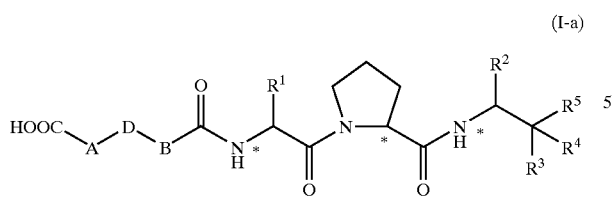

(I-a)

wherein * means that the carbon atom marked with * is an asymmetric carbon atom, A and B are the same or different and each is a lower alkylene group being optionally substituted by an oxo group, D is a heteromonocyclic or heterobicyclic group of the following formula:

wherein $D^1$ is a methylene group or an ethylene group, and these groups may optionally be substituted by an oxo group, Ring G is a 5- to 14-membered, saturated or unsaturated, heteromonocyclic or heterobicyclic group optionally having other heteroatoms selected from a nitrogen atom, an oxygen atom and/or a sulfur atom, and said heterocyclic group being optionally substituted by a substituent $T^1$, in which $T^1$ is the same or different 1 to 3 groups selected from (i) an oxo group,
(ii) a substituted or unsubstituted lower alkyl group,
(iii) a substituted or unsubstituted amino group,
(iv) a substituted or unsubstituted carbamoyl group,
(v) a carboxyl group or a lower alkoxycarbonyl group,
(vi) a phenyl group being optionally substituted by a halogen atom, a lower alkoxy group or a lower alkyl group, and
(vii) a substituted or unsubstituted lower alkylcarbonyl group, $R^1$ and $R^2$ are the same or different and each is a lower alkyl group, $R^3$ and $R^4$ are different from each other, and each is a hydrogen atom or a hydroxy group, or both combine together to form an oxo group, $R^5$ is a group of the formula:

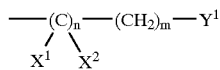

wherein $X^1$ and $X^2$ are a halogen atom, $Y^1$ is a hydrogen atom, a halogen atom, a lower alkoxycarbonyl group, a lower alkylaminocarbonyl group, an aralkylaminocarbonyl group, an aralkyloxycarbonyl group, a lower alkylcarbonyl group, or an aralkylcarbonyl group, or a group of the following formula:

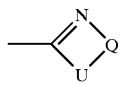

wherein U is an oxygen atom or a sulfur atom, Q is a vinylene group or an orthophenylene group being optionally substituted by $T^2$, $T^2$ is 1 to 3 groups selected from a halogen-substituted or unsubstituted lower alkyl group, a lower alkoxy group, a lower alkylsulfonyl group, a lower alkylcarbonyloxy group and an amino group being optionally substituted by a lower alkyl group, n is 0, 1 or 2, and m is an integer of 0 to 5.

Hereinafter, the present compounds (I-a) are explained in more detail.

Among the compounds of the above formula (I-a), the compound (I-a) wherein $R^3$ and $R^4$ combine together to form an oxo group (hereinafter, occasionally referred to the ketone compound) exhibits an excellent elastase inhibitory activity. The partial structure of the formula (I-a) represented by HOOC-A-D-B- greatly contributes so that to exhibit such excellent properties of the present compound (I-a). In addition, the present compounds can be distinguished from the above mentioned known compounds in this specific partial structure.

Therefore, the primary characteristic of the chemical structure of the present compounds (I-a) is the above-mentioned specific partial structure. The secondary characteristic of the chemical structure of the present compounds (I-a) is a combination of the above-mentioned specific partial structure and the rest of the structure.

Among the compounds of the above formula (I-a), the compound (I-a) wherein $R^3$ and $R^4$ are different from each other and each is a hydrogen atom or a hydroxy group (hereinafter, referred to the OH compound) is useful as an intermediate for directly preparing the above compound (the ketone compound) which is an elastase inhibitor.

The definition for each substituent is explained below.

The term "lower" means that a group accompanied by this term is a group having 1 to 5 carbon atoms, preferably 1 to 4 carbon atoms, unless otherwise specified. Therefore, the "lower alkyl group" is a straight chain or branched chain hydrocarbon having 1 to 5 carbon atoms, such as methyl, ethyl, propyl, isopropyl, butyl, tert-butyl, pentyl, etc. The "lower alkylene group" is a group wherein one hydrogen atom is removed from the above-mentioned lower alkyl group. The "lower alkoxy group" is a lower alkyloxy group wherein the lower alkyl moiety is the above-mentioned lower alkyl group, such as methoxy, ethoxy, butoxy, etc.

The "lower alkylene group being optionally substituted by an oxo group" for A and B is a lower alkylene group such as methylene, ethylene, propylene, etc., or a lower alkylene group being substituted by an oxo group such as a group of the formula: —$CH_2CO$— or a malonyl group of the formula: —$COCH_2CO$—, and methylene is preferable.

D of the above formula (I-a) is defined above, but will be explained in more detail.

D is the above-mentioned heteromonocyclic or heterobicyclic group, and the heteromonocyclic group is more preferable. In addition, the number of the other heteroatoms within the ring such as a nitrogen atom, an oxygen atom or a sulfur atom is 3 or less when Ring G is a monocyclic group, and when Ring G is a bicyclic group, then the number of the other heteroatoms within the ring is 5 or less. The size of the ring is not specified, but when the ring is a monocyclic group, then it is usually a 4- to 9-membered ring, preferably a 5- or 6-membered ring. When the ring is a bicyclic group, then the ring condensed with the ring containing —N-$D^1$-N— is usually a 5- or 6-membered ring. These heterocyclic groups may be either saturated or unsaturated one.

Among the substituents $T^1$ of Ring G, the substituted lower alkyl group is a lower alkyl group having 1 or more substituents selected from an amino group, a lower alkylamino group, a carboxyl group, a phenyl group or phenylamino group (these phenyl moieties may be optionally substituted by a halogen atom, a lower alkoxy group or a lower alkyl group) and a lower alkylcarbonyl group; the substituted amino group is an amino group being substituted by 1 or 2 groups selected from a lower alkyl group, a phenyl group (said phenyl group being optionally substituted by a halogen atom, a lower alkoxy group or a lower alkyl group) and a lower alkylcarbonyl group; the substituted carbamoyl group is a carbamoyl group wherein the amino moiety has 1 or 2 substituents selected from a lower alkyl group, a phenyl group (said phenyl group being optionally substituted by a halogen atom, a lower alkoxy group or a lower alkyl group) and a lower alkylcarbonyl group; the substituted lower alkylcarbonyl group is a lower alkyl-carbonyl group wherein the lower alkyl moiety has one or more substituents selected from an amino group, a lower alkylamino group, a carboxyl group, a phenyl group (said phenyl group being optionally substituted by a halogen atom, a lower alkoxy group, or a lower alkyl group) and a lower alkylcarbonyl group.

The suitable substituent $T^1$ of Ring G is, for example, an oxo group, a lower alkyl group, an amino-lower alkyl group, a mono- or di-lower alkylamino-lower alkyl group, a phenyl-lower alkyl group, a phenylamino-lower alkyl group, a carboxy-lower alkyl group, an amino group, a mono- or di-lower alkylamino group, a phenylamino group, a phenyl group, a lower alkylphenyl group, a carboxyl group, a carbamoyl group, a mono- or di-lower alkylcarbamoyl group, etc. The phenyl group as mentioned herein may be substituted by a halogen atom, a lower alkoxy group or a lower alkyl group.

The preferable groups of the formula: -A-D-B- are groups of the following formula:

wherein A, B and $D^1$ are as defined above, Ring $G^1$ is the same heteromonocyclic groups for Ring G as mentioned above. That is, Ring $G^1$ is a 5- to 9-membered, preferably a 5- or 6-membered, saturated or unsaturated heteromonocyclic group having optionally other 1 to 3 heteroatoms selected from a nitrogen atom, an oxygen atom and/or a sulfur atom, and said heteromonocyclic group may have 1 to 3 same substituents $T^1$ as mentioned above.

Moreover, the preferable groups of the formula: -A-D-B- are groups of the following formula:

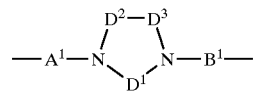

wherein $A^1$ is a methylene group or a group of the formula: —CH$_2$CO—, $B^1$ is a methylene group or a group of the formula: —COCH$_2$—, $D^2$ and $D^3$ are the same or different and each is a vinylene group being optionally substituted by a lower alkyl group, or a methylene group being optionally substituted by an oxo group or a lower alkyl group, $D^1$ is the same as defined above, provided that both $D^2$ and $D^3$ should not simultaneously be a vinylene group being optionally substituted by a lower alkyl group.

Next, the groups of the formula: HOOC-A-D-B- are exemplified below. Among them, the groups of (1) to (6), especially the groups of (1) and (2) are preferable.

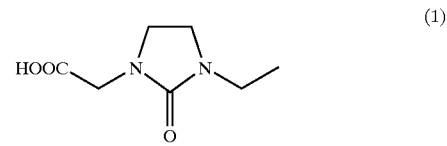

(1)

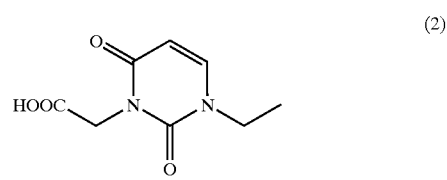

(2)

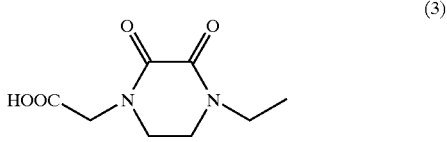

(3)

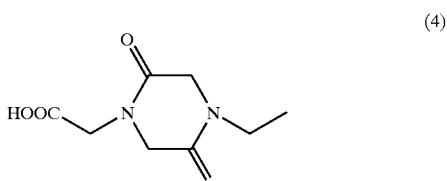

(4)

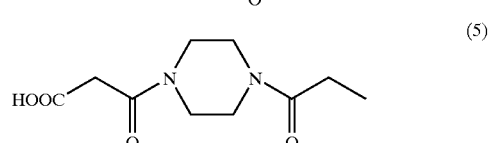

(5)

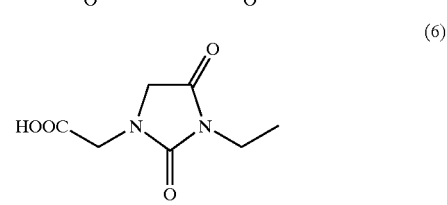

(6)

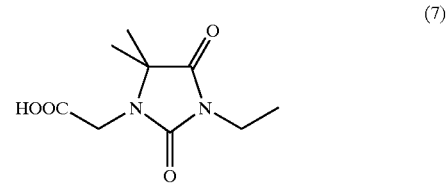

(7)

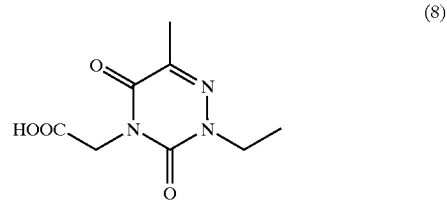

(8)

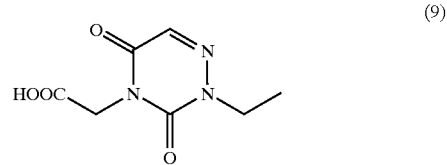

(9)

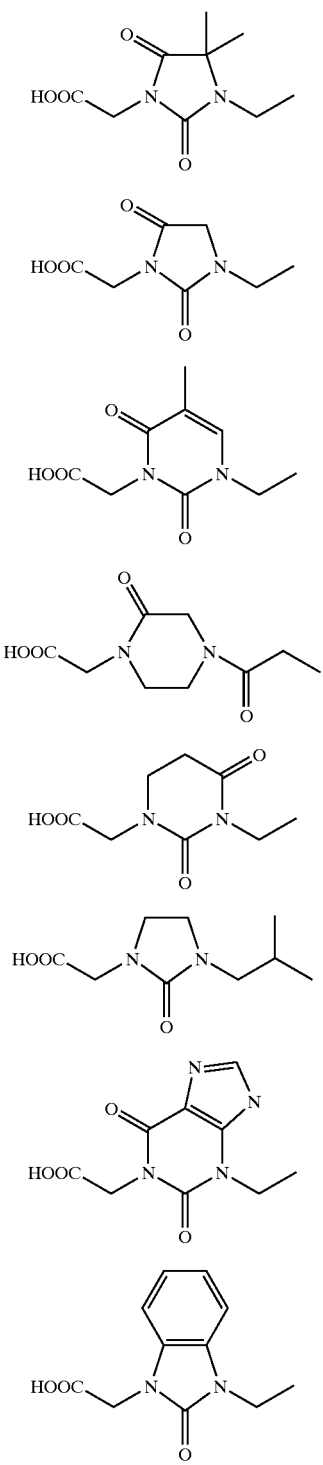

As the "lower alkyl group" for $R^1$ and $R^2$, an isopropyl group is most preferable, and methyl, ethyl, propyl, butyl, sec-butyl, tert-butyl, 2-methylbutyl, etc. can be exemplified. In addition, the carbon atom to which $R^1$ and $R^2$ bond is an asymmetric carbon atom.

$R^5$ may be any groups within the scope of the above formula, for example, a lower alkylcarbonyl group such as n-butylcarbonyl group; an aralkylcarbonyl group such as benzylcarbonyl group; a lower alkoxycarbonyl group such as methoxycarbonyl group or n-propyloxy-carbonyl group; an aralkyloxycarbonyl group such as benzyloxycarbonyl group; a lower alkylcarbonyldifluoromethyl group such as n-propylcarbonyldifluoromethyl group; an aralkylcarbonyldifluoromethyl group such as benzylcarbonyldifluoromethyl group; a lower alkyloxy-carbonyldifluoromethyl group such as n-propyloxycarbonyldifluoro-methyl group; an aralkyloxycarbonyldifluoromethyl group such as benzyloxycarbonyldifluoromethyl group; a lower alkylaminocarbonyldifluoromethyl group such as n-propylaminocarbonyldifluoromethyl group; an aralkylaminocarbonyldifluoromethyl group such as benzylaminocarbonyldifluoromethyl group; a lower alkylaminocarbonyl group such as n-propylaminocarbonyl group; an aralkylaminocarbonyl group such as benzylaminocarbonyl group; a halogeno-lower alkyl group such as trifluoromethyl group or monochloromethyl group; a hydrogen atom; a substituted or unsubstituted, heteromonocyclic or heterobicyclic group containing a nitrogen atom and an oxygen atom or a sulfur atom such as a substituted or unsubstituted benzoxazolyl group. Especially preferable group for $R^5$ is a trifluoromethyl group, a benzoxazolyl group or a benzylaminocarbonyl group.

As mentioned above, a compound having an elastase inhibitory activity is the compound wherein $R^3$ and $R^4$ combine together to form an oxo group, i.e., the ketone compound, and the compound wherein one of $R^3$ and $R^4$ is a hydrogen atom, and the other is a hydroxy group, i.e., the OH compound, is an intermediate for directly preparing the ketone compound. That is, among the present compounds (I-a), the compound having an elastase inhibitory activity is a ketone compound of the following formula (I-b).

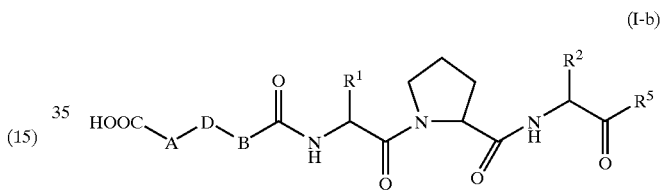

wherein A, B, D, $R^1$, $R^2$ and $R^5$ are as defined above. From the viewpoint of the degree of the potency of elastase inhibitory activity and the solubility in an aqueous solvent, the present compounds being more suitable for an elastase inhibitor are compounds of the following formula (I-c) and a pharmaceutically acceptable salt thereof.

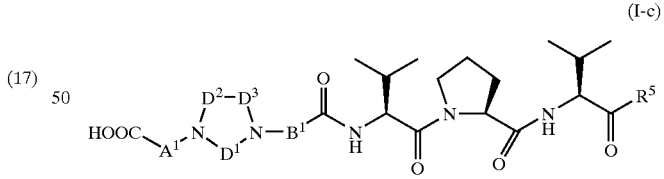

wherein $A^1$, $B^1$, $D^1$, $D^2$, $D^3$ and $R^5$ are as defined above, provided that both $D^2$ and $D^3$ should not simultaneously be a vinylene group being optionally substituted by a lower alkyl group.

Among the compounds of the above formula (I-c), preferable compounds are the following compounds and a pharmaceutically acceptable salt thereof. Most especially, Compound 1 and Compound 2 and a pharmaceutically acceptable salt thereof are especially preferable.

Compound 1:
2-(3-carboxymethyl-2-oxo-1-imidazolidinyl)acetyl-L-valyl-N-[(1S)-3,3,3-trifluoro-1-isopropyl-2-oxopropyl]-L-prolinamide;

Compound 2:
2-(3-carboxymethyl-2,4-dioxo-1-pyrimidinyl)acetyl-L-valyl-N-[(1S)-2-(2-benzoxazolyl)-1-isopropyl-2-oxoethyl]-L-prolinamide;
Compound 3:
2-(4-carboxymethyl-2,3-dioxo-1-piperazinyl)acetyl-L-valyl-N-[(1S)-2-(2-benzoxazolyl)-1-isopropyl-2-oxoethyl]-L-prolinamide;
Compound 4:
2-(3-carboxymethyl-2,4-dioxo-1-pyrimidinyl)acetyl-L-valyl-N-[(1S)-3-benzylamino-1-isopropyl-2,3-dioxopropyl]-L-prolinamide,
Compound 5:
2-(4-carboxymethyl-2,5-dioxo-1-piperazinyl)acetyl-L-valyl-N-[(1S)-2-(2-benzoxazolyl)-1-isopropyl-2-oxoethyl]-L-prolinamide;
Compound 6:
2-(3-carboxymethyl-2,5-dioxo-1-imidazolidinyl)acetyl-L-valyl-N-[(1S)-3,3,3-trifluoro-1-isopropyl-2-oxopropyl]-L-prolinamide;
Compound 7:
[[4-(2-carboxyacetyl)-1-piperazinyl]malonyl]-L-valyl-N-[(1S)-2-(2-benzoxazolyl)-1-isopropyl-2-oxoethyl]-L-prolinamide In addition to the above compounds, as a compound included within the scope of the formula (I-a), ones disclosed in Experiments and Examples as mentioned below can be exemplified, and further the following compounds, their esters, and salts thereof are also exemplified.

2-(3-carboxymethyl-2-oxo-1-imidazolidinyl)acetyl-L-valyl-N-[(1S)-(3-butyl-1-isopropyl-2,3-dioxopropyl)]-L-prolinamide;
2-(3-carboxymethyl-2-oxo-1-imidazolidinyl)acetyl-L-valyl-N-[(1S)-(3-benzyl-1-isopropyl-2,3-dioxopropyl)]-L-prolinamide;
2-(3-carboxymethyl-2,4-dioxo-1-pyrimidinyl)acetyl-L-valyl-N-[(1S)-(3-propoxy-1-isopropyl-2,3-dioxopropyl)]-L-prolinamide;
2-(3-carboxymethyl-2-oxo-1-imidazolidinyl)acetyl-L-valyl-N-[(1S)-(3-benzyloxy-1-isopropyl-2,3-dioxopropyl)]-L-prolinamide;
2-(3-carboxymethyl-2-oxo-1-imidazolidinyl)acetyl-L-valyl-N-[(1S)-(3,3-difluoro-4-butyl-1-isopropyl-2,4-dioxobutyl)]-L-prolinamide;
2-(4-carboxymethyl-2,5-dioxo-1-piperazinyl)acetyl-L-valyl-N-[(1S)-(3,3-difluoro-4-benzyl-1-isopropyl-2,4-dioxobutyl)]-L-prolinamide;
2-(3-carboxymethyl-2,4-dioxo-1-pyrimidinyl)acetyl-L-valyl-N-[(1S)-(3,3-difluoro-4-propoxy-1-isopropyl-2,4-dioxobutyl)]-L-prolinamide;
2-(3-carboxymethyl-2,5-dioxo-1-imidazolidinyl)acetyl-L-valyl-N-[(1S)-(3,3-difluoro-4-benzyloxy-1-isopropyl-2,4-dioxobutyl)]-L-prolinamide;
2-(3-carboxymethyl-2-oxo-1-imidazolidinyl)acetyl-L-valyl-N-[(1S)-(3,3-difluoro-4-propylamino-1-isopropyl-2,4-dioxobutyl)]-L-prolinamide;
2-(3-carboxymethyl-2,5-dioxo-1-imidazolidinyl)acetyl-L-valyl-N-[(1S)-(3,3-difluoro-4-benzylamino-1-isopropyl-2,4-dioxobutyl)]-L-prolinamide;
2-(3-carboxymethyl-2,5-dioxo-1-imidazolidinyl)acetyl-L-valyl-N-[(1S)-(1-isopropyl-2-oxoethyl)]-L-prolinamide;
2-(3-carboxymethyl-2,5-dioxo-1-imidazolidinyl)acetyl-L-valyl-N-[(1S)-(3-chloro-1-isopropyl-2-oxopropyl)]-L-prolinamide;
2-(3,4-biscarboxymethyl-2,5-dioxo-1-imidazolidinyl)acetyl-L-valyl-N-[(1S)-(3,3,3-trifluoro-1-isopropyl-2-oxopropyl)]-L-prolinamide;
2-(3-benzyl-4-carboxymethyl-2,5-dioxo-1-piperazinyl)acetyl-L-valyl-N-[(1S)-(3,3,3-trifluoro-1-isopropyl-2-oxopropyl)]-L-prolinamide;
2-(5-amino-3-carboxymethyl-2,4,6-trioxo-1-pyrimidinyl)acetyl-L-valyl-N-[(1S)-(3,3,3-trifluoro-1-isopropyl-2-oxopropyl)]-L-prolinamide;
2-(3-carboxymethyl-6-diethylamino-2,4-dioxo-1-pyrimidinyl)acetyl-L-valyl-N-[(1S)-(3,3,3-trifluoro-1-isopropyl-2-oxopropyl)]-L-prolinamide;
2-(5-amino-3-carboxymethyl-2,4,6-trioxo-1-pyrimidinyl)acetyl-L-valyl-N-[(1S)-(3,3,3-trifluoro-1-isopropyl-2-oxopropyl)]-L-prolinamide;
2-(3-carboxymethyl-4-phenylamino-2,6-dioxo-1-pyrimidinyl)acetyl-L-valyl-N-[(1S)-(3,3,3-trifluoro-1-isopropyl-2-oxopropyl)]-L-prolinamide;
2-(5-aminomethyl-3-carboxymethyl-2,6-dioxo-1-pyrimidinyl)acetyl-L-valyl-N-[(1S)-(3,3,3-trifluoro-1-isopropyl-2-oxopropyl)]-L-prolinamide;
2-(3-carboxymethyl-5-(dimethylaminomethyl)-2,6-dioxo-1-pyrimidinyl)-acetyl-L-valyl-N-[(1S)-(3,3,3-trifluoro-1-isopropyl-2-oxopropyl)]-L-prolinamide;
2-(3-carboxymethyl-5-phenylaminomethyl-2,6-dioxo-1-pyrimidinyl)-acetyl-L-valyl-N-[(1S)-(3,3,3-trifluoro-1-isopropyl-2-oxopropyl)]-L-prolinamide;
2-(4-carboxy-3-carboxymethyl-2,6-dioxo-1-pyrimidinyl)acetyl-L-valyl-N-[(1S)-(3,3,3-trifluoro-1-isopropyl-2-oxopropyl)]-L-prolinamide;
2-(3,4-biscarboxymethyl-2,6-dioxo-1-pyrimidinyl)acetyl-L-valyl-H-[(1S)-(3,3,3-trifluoro-1-isopropyl-2-oxopropyl)]-L-prolinamide;
2-[3-carboxymethyl-4-(4-methylphenyl)-4-phenyl-2-oxo-1-imidazolidin-yl]acetyl-L-valyl-N-[(1S)-(3,3,3-trifluoro-1-isopropyl-2-oxopropyl)]-L-prolinamide;
2-(4-carboxymethyl-2-phenyl-3,9-dioxo-1,4-benzodiazepin-1-yl)acetyl-L-valyl-N-[(1S)-(3,3,3-trifluoro-1-isopropyl-2-oxopropyl)]-L-prolinamide;
2-[3-carboxymethyl-4-(N,N-dimethylcarbamoyl)-1-imidazolidinyl]acetyl-L-valyl-N-[(1S)-(3,3,3-trifluoro-1-isopropyl-2-oxopropyl)]-L-prolinamide;
4-(3-carboxymethyl-2-oxo-1-imidazolidinyl)isovalelyl-L-valyl-N-[(1S)-(3)3,3-trifluoro-1-isopropyl-2-oxopropyl)]-L-prolinamide;
2-(3-carboxymethyl-2-oxo-1-benzimidazolidinyl)acetyl-L-valyl-N-[(1S)-(3,3,3-trifluoro-1-isopropyl-2-oxopropyl)]-L-prolinamide.

The ester of the present compound (I-a) may be any one having a conventional ester residue, for example, a lower alkyl ester such as methyl ester, ethyl ester, propyl ester, tert-butyl ester; a lower alkoxy-lower alkyl ester such as methoxymethyl ester; an aralkyloxy-lower alkyl ester such as benzyloxymethyl ester; a benzyl ester; a lower alkyl ester being substituted by a monovalent 5- or 6-mebered, saturated or unsaturated monocyclic group having optionally 1 or 2 heteroatoms such as pyridylmethyl ester, 2-morpholinylmethyl ester, 3-furylmethyl ester; a phenyl ester being optionally substituted by a halogen atom, a lower alkyl group, a lower alkoxy group, a nitro group, a lower alkyl-amino group and/or a lower alkoxycarbonyl group.

The salt of the present compound (I-a) is not necessarily specified, but preferably a pharmaceutically acceptable salt, for example, a salt with an organic base such as trimethylamine, triethylamine, N-methylmorpholine; and a salt with an inorganic metal such as sodium or potassium. In addition, some of the present compounds may form an acid addition salt. Such an acid addition salt may be a salt with an organic acid such as tartaric acid, fumaric acid, acetic acid, lactic acid, succinic acid, methanesulfonic acid, maleic acid, malonic acid, gluconic acid, an amino acid such as aspartic acid, or a salt with an inorganic acid such as hydrochloric acid, phosphoric acid, etc.

The present compound (I-a) may occasionally exist in the form of a hydrate or a solvate. In addition, the present compound (I-a) may exist in the form of an optically active compound or a stereoisomer, or a mixture thereof, and the present invention includes all of these forms.

The present invention also relates to a human neutrophilic elastase inhibitor containing as the active ingredient a water-soluble compound of the present invention. By the following Experiments, the inhibitory activity of the present compound against human neutrophilic elastase is illustrated below.

Experiment 1: Human Neutrophilic Elastase Inhibitory Activity

In the present experiment, the inhibitory activity of the present invention against human neutrophilic elastase was studied in vitro.

Human neutrophilic elastase (Sigma) was dissolved in a HEPES Buffer (133 mM, pH 7.5) containing 1.9 M sodium chloride, 0.38% polyethylene glycol 6000 and 0.0019% Bri j-35 at a final concentration of 1.9 mU/ml. The resulting solution (210 µl) was mixed with a $10^{-8}$–$10^{-5}$ M solution of the present compound (40 µl), and the mixture was pre-incubated at 37° C. for 6 minutes. To this solution, 4 mM succinyl-alanyl-prolyl-alanine 4-methyl-coumaryl-7-amide (substrate solution, Peptide Institute Inc.) (50 µl) and distilled water (100 µl) were added, and the mixture was further reacted at 37° C. for 20 minutes. The concentration of the 7-amino-4-methylcoumarine thus obtained was measured fluorimetrically by monitoring at an excitation wave length of 380 nm and a fluorescent wave length of 460 nm.

The above "Bri j-35" means polyoxyethylene (23) lauryl ether, and the "HEPES" means N-(2-hydroxyethyl) piperazine-N'-(2-ethane-sulfonic acid).

The elastase inhibitory activity (inhibitory rate) was calculated according to the following equation, and the 50% inhibitory concentration ($IC_{50}$ value) was obtained from the concentration-inhibitory rate curve of the present compound. The results are shown in Table 1.

In the following equation, A means the intensity of fluorescence when a present compound is added, and B means the intensity of fluorescence when a present compound is not added.

Inhibitory Rate (%)=(1−A/B)×100

TABLE 1

Elastase Inhibitory Activity

| Comp. No. | ROOC—A—D—B— | R⁵ | $IC_{50}$ (µM) |
|---|---|---|---|
| I-b-1 | HOOC-CH₂-(imidazolidinone-N,N')-Et | CF₃ | 0.010 |
| I-b-2 | HOOC-CH₂-(uracil-N,N')-Et | benzoxazol-2-yl | 0.024 |
| I-b-3 | HOOC-CH₂-(uracil-N,N')-Et | CH₂NHC(O)-benzyl | 0.021 |
| I-b-4 | HOOC-CH₂-(piperazine-2,3-dione-N,N')-Et | benzoxazol-2-yl | 0.030 |

TABLE 1-continued

Elastase Inhibitory Activity

| Comp. No. | ROOC—A—D—B— | $R^5$ | $IC_{50}$ (μM) |
|---|---|---|---|
| I-b-5 | HOOC-CH2-N(piperazine-2,5-dione)-N-Et | 2-benzoxazolyl | 0.062 |
| I-b-7 | HOOC-CH2-N(imidazolidine-2,4-dione)-N-Et | $CF_3$ | 0.082 |
| I-b-8 | HOOC-CH2-C(O)-N(piperazine)-N-C(O)-Et | 2-benzoxazolyl | 0.067 |
| I-b-9 | HOOC-CH2-N(6-methyl-1,2,4-triazine-3,5-dione)-N-Et | 2-benzoxazolyl | 0.027 |
| I-b-10 | HOOC-CH2-N(piperazin-2-one)-N-C(O)-Et | 2-benzoxazolyl | 0.045 |
| I-b-11 | HOOC-CH2-N(uracil)-N-Et | $COOCH_3$ | 0.007 |
| I-b-12 | HOOC-CH2-N(piperazine-2,3-dione)-N-Et | -C(O)NH-CH2-Ph | 0.020 |
| I-b-13 | HOOC-CH2-N(imidazolidine-2,4-dione)-N-Et | 2-benzoxazolyl | 0.042 |

TABLE 1-continued

Elastase Inhibitory Activity

| Comp. No. | ROOC—A—D—B— | R⁵ | IC₅₀ (μM) |
|---|---|---|---|
| I-b-14 | HOOC-CH₂-[1-(imidazolidine-2,4-dione)-3-ethyl] | 2-benzoxazolyl | 0.035 |
| I-b-15 | HOOC-CH₂-[1-(5-methyluracil)-3-ethyl] | 2-benzoxazolyl | 0.014 |
| I-b-16 | HOOC-CH₂-[1-(uracil)-3-ethyl] | 2-benzoxazolyl | 0.027 |
| I-b-17 | HOOC-CH₂-[1-(5,5-dimethylimidazolidine-2,4-dione)-3-ethyl] | 2-benzoxazolyl | 0.023 |
| I-b-18 | HOOC-CH₂-[1-(imidazolidin-2-one)-3-ethyl] | 2-benzoxazolyl | 0.017 |
| I-b-19 | HOOC-CH₂-[1-(4,4-dimethylimidazolidine-2,5-dione)-3-ethyl] | 2-benzoxazolyl | 0.005 |
| I-b-20 | HOOC-CH₂-[1-(tetrahydropyrimidine-2,4-dione)-3-ethyl] | 2-benzoxazolyl | 0.033 |
| I-b-21 | HOOC-CH₂-[1-(piperazine-2,3-dione)-4-ethyl] | COOCH₃ | 0.006 |

TABLE 1-continued

Elastase Inhibitory Activity

ROOC-A-D-B-C(=O)-NH-Val-Pro-NH-CH(iPr)-C(=O)-R⁵

| Comp. No. | ROOC—A—D—B— | R⁵ | IC$_{50}$ ($\mu$M) |
|---|---|---|---|
| I-b-22 | HOOC-CH$_2$-N(triazinedione-ethyl) | 2-benzoxazolyl | 0.043 |
| I-b-23 | HOOC-CH$_2$-N(pyrimidinedione-ethyl) | CF$_3$ | 0.028 |
| Control (a) | (H$_3$C)$_3$C-C(=O)-O-C$_6$H$_4$-SO$_2$-NH-C$_6$H$_4$-C(=O)-NH-CH$_2$-COOH | | 0.017 |
| Control (b) | uracil-CH$_2$-C(=O)-NH-Val-Pro-NH-CH(iPr)-C(=O)-CF$_3$ | | 1.0 |

As is shown in Table 1, the concentration of the present invention to be required to achieve 50% human neutrophilic elastase inhibition (i.e., IC$_{50}$) is not more than 0.082 $\mu$M, and some of the present compounds showed an IC$_{50}$ almost equal to that of the control compound (a). As mentioned before, the control compound (a) is disclosed in U.S. Pat. No. 5,017,610, Example 2 (63), and it is a human neutrophilic elastase inhibitor being under development, of which compound code has been known as ONO-5046.

In addition, the inhibitory activities of the present invention against human neutrophilic elastase (IC$_{50}$) are much more potent than that of the control compound (b) as disclosed in Table 1. The control compound (b) is a novel compound, but it does not have a group of the formula: HOOC-A-, and hence, it cannot be included within the scope of the formula (I-a).

Experiment 2: Inhibitory Activity on Pulmonary Hemorrhage Induced by Human Neutrophilic Elastase When human neutrophilic elastase is administered intratracheally to a hamster, the hemorrhage is induced in the lung. Hemoglobin is detected in the broncho-alveolar lavage fluid, which is obtained by washing the lung via bronchi at a fixed period after the elastase administration. In order to examine how much this hemorrhage can be inhibited by the present compound, this experiment was carried out by measuring the concentration of this hemoglobin.

Hamsters (male Syrian strain, 8–10 weeks old) were grouped into the following three groups (5 animals per group), and the following treatment was carried out on each group.

(A) Vehicle-Treated Control Group (Non-Treatment Group):

Physiological saline solution (0.2 ml) was administered intratracheally to the hamsters, and one hour thereafter, the alveolus was bronchially washed five times with physiological saline solutions (each 2.5 ml), and then, the concentration of hemoglobin in the broncho-alveolar lavage fluid (12.5 ml) was measured by the absorbance at 414 nm. The result of the measurement was counted as A.

(B) Human Neutrophilic Elastase-Treated Group (Without the Present Compound):

Human neutrophilc elastase (25 units, manufactured by Elastin Products, Inc.) was dissolved in physiological saline solution (0.2 ml), and the solution thus obtained was administered to the hamsters at the bronchial tube to induce the pulmonary hemorrhage. One hour after the administration of elastase, the concentration of hemoglobin in the broncho-alveolar lavage fluid was measured in the same manner as in Group (A). The result of the measurement was counted as B.

(C) Human Neutrophilic Elastase-Treated Group (with the Present Compound):

A fixed amount of the present compound was administered to the hamsters in the form of a phosphate-buffered saline solution (pH 7.4) in the manner as described below.

Then, human neutrophilic elastase was administered to the hamsters in the same manner as the above. One hour after the administration of elastase, the concentration of hemoglobin in the washing of the broncho-alveolar lavage was measured in the same manner as in Group (A). The result of the measurement was counted as C.

Administration Method of the Present Compound:

The administration of the present compound to the hamsters was carried out by two kinds of methods. One of them is a method of intravenous bolus-administration of the solution containing the present compound 5 minutes prior to the elastase administration. Another method is a method of intravenous infusion of the solution containing the present compound for a period of 70 minutes beginning at 10 minutes prior to the elastase administration.

Hemorrhage inhibitory rate (%) was calculated according to the following equation (average among 5 cases). In the equation, each A, B and C means the above meaning respectively, and the experiment data are shown in Table 2.

$$\text{Hemorrhage Inhibitory Rate (\%)} = [1-(C-A)/(B-A)] \times 100$$

TABLE 2

Elastase-induced pulmonary hemorrhage inhibitory activity

| Comp. No. | Intravenous bolus administration Dose (mg/kg) | | | Intravenous-infusion Dose (mg/kg/hr) | | |
|---|---|---|---|---|---|---|
| | (30) | (10) | (3) | (10) | (3) | (1) |
| I-b-1 | — | 97 | 61 | 94 | 71 | 54 |
| I-b-2 | 97 | 66 | 24 | 93 | 62 | 50 |
| I-b-3 | — | 77 | 20 | 90 | 78 | 32 |
| I-b-4 | — | 88 | 57 | 95 | 76 | 41 |
| I-b-5 | — | 67 | 20 | 90 | 73 | 55 |
| I-b-7 | — | 64 | 50 | 72 | 53 | 51 |
| I-b-8 | — | 78 | 63 | — | 69 | 33 |
| I-b-9 | — | 48 | — | — | — | — |
| I-b-10 | — | 76 | 32 | 92 | 69 | 52 |
| 1-b-11 | — | 93 | 61 | 94 | 43 | 32 |
| I-b-12 | — | 99 | 70 | 89 | 47 | 31 |
| I-b-13 | 91 | 67 | 32 | 78 | 44 | — |
| I-b-14 | 81 | 72 | 37 | 53 | 57 | 39 |
| Control (a) | (200) | (100) | (30) | (100) | (30) | (10) |
| | 99 | 74 | 28 | 60 | 43 | 18 |

The figures in Table indicate hemorrhage inhibitory rates (%).

However, the figures in parentheses indicate dosages.

As is shown in Table 2, the human neutrophilic elastase-induced pulmonary hemorrhage inhibitory activity of the present compounds is far higher than that of the control compound (a).

Experiment 3: Acute Toxicity Test in Mice

The present compound was dissolved in phosphate buffered physiological saline solution (pH 7.4), and the solution was injected to 7-weeks old male Std:ddy mice (6 animals per group) at the tail vein. Twenty-four hours after the administration, the animals were observed if dead or alive. The results thereof are shown in Table 3.

TABLE 3

Acute Toxicity

| Comp. No. | Dose of intravenous administration (mg/kg) | Livability* |
|---|---|---|
| I-b-1 | 300 | 6/6 |
| I-b-2 | 300 | 6/6 |
| I-b-3 | 300 | 6/6 |

*Number of survived animals/number of tested animals

*: Number of survived animals/number of tested animals

Experiment 4: Solubility in Aqueous Solvent

The solubility in an aqueous solvent of the present compound was measured, and the results as shown in Table 4 were obtained. The pH value in Table 4 is a pH value of a solution of the present compound in distilled water.

TABLE 4

Solubility (25° C.)

| | Solubility (mg/ml) | |
|---|---|---|
| Comp. No. | 0.1 M Phosphate buffer (pH 7.4) | Water |
| I-b-1 | >1000 | >1000 (pH 2.3) |
| I-b-2 | >100 | 5.0 (pH 2.8) |
| I-b-3 | >100 | 8.7 (pH 2.6) |
| Control (a) | about 20 | 0.012 (pH 4.7) |

As is shown in Table 4, the solubilities in aqueous solvent of the present compounds are more than 100 mg/ml, which are more than that of the control compound (a).

From the results of the above Experiments, the present compound is an excellent water-soluble elastase inhibitor, and is useful in the treatment of various diseases, especially acute pulmonary diseases.

The dosage of the present compounds varies according to the routes of the administration, conditions and ages of the patients, but it is usually in the range of about 2 to 5000 mg/60 kg of body weight/day, preferably in the range of about 10 to 2000 mg/60 kg of body weight/day, especially preferably in the range of 30 to 1500 mg/60 kg of body weight/day. The present compounds may be administered orally, but preferably administered parentally, especially intravenously.

The present compound may be administered in the form of a conventional pharmaceutical preparation, and these preparations may be prepared by mixing the present compound with a conventional pharmaceutically acceptable carrier or diluent. For example, the pharmaceutically acceptable carrier or diluent for a liquid preparation for parental administration includes essentially vehicles such as water, physiological saline solution, and in addition thereto, includes optionally other auxiliary agents such as isotonic agents, anesthetic agents, pH adjusting agents, buffering agents, preservatives, etc.

Liquid preparation such as injection may be prepared by dissolving the present compound in a vehicle such as a physiological saline solution for injection, and if necessary, followed by mixing other auxiliary agents before or after the dissolution of the present compound. Lyophilized preparations may be prepared by lyophilizing such a liquid preparation, and it is re-dissolved when used.

In addition, the present invention relates to the compound of the formula (II) or a salt thereof.

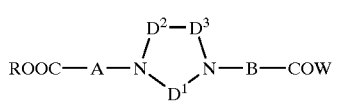
(II)

wherein A, B, $D^1$, $D^2$ and $D^3$ are as defined above, R is a protecting group for carboxyl group, W is a hydroxy group, a halogen atom or an active carboxylic acid ester such as a lower alkylcarbonyloxy group, provided that one of A, B, $D^1$, $D^2$ and $D^3$ is a group being substituted by an oxo group, and that both $D^2$ and $D^3$ should not simultaneously be a vinylene group being optionally substituted by a lower alkyl group.

The processes for preparing the present compounds (I-a) and (II) are explained below.

The structure of the present compound (I-a) is a tripeptide derivative wherein two amino acids bond to one proline at each end thereof. Therefore, the present compound (I-a) may be prepared mainly by amidation reaction.

For example, the present compounds (I-a) and (II) may be prepared by the following reaction scheme (Reaction Scheme 1) as mentioned below.

The protecting group R for carboxyl group in Reaction Scheme 1 may be any one that does not disturb the desired main reaction and can be easily removed without breaking the other partial structure when desired. The protecting group R for carboxyl group can be classified into two categories in terms of the methods for removal thereof. One of the methods for removal thereof is acid-base decomposition, and the other one is hydrogenolysis. The protecting group for carboxyl group being able to be removed by acid-base decomposition is, for example, methyl, ethyl, tert-butyl, trityl, methoxymethyl, benzyl, phenyl, phenacyl, etc., and the protecting group for carboxyl group being able to be removed by hydrogenolysis is, for example, benzyl, trityl, benzyloxymethyl, etc.

Although W in Reaction Scheme 1 is as explained above, W is preferably a hydroxy group or a halogen atom, $X^3$ is a halogen atom, and other symbols are as defined above.

Reaction Scheme 1

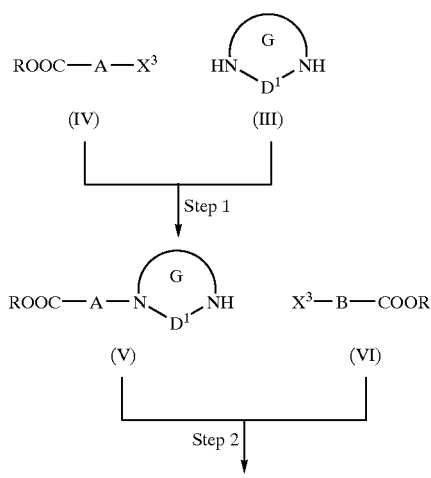

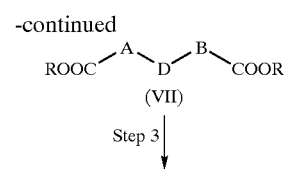
(VII)

Step 3

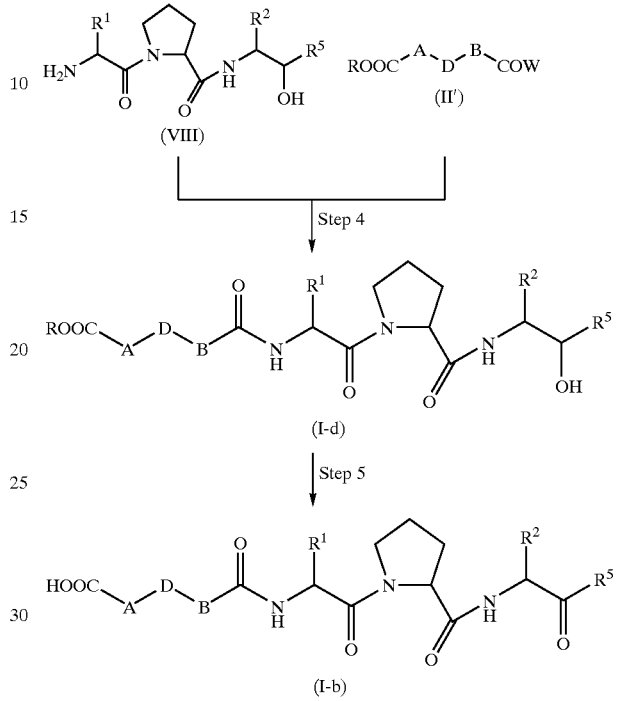

In the above Reaction Scheme 1, Step 1 is a step of reacting the known compounds (III) and (IV) to give the compound MV. This step is 3 carried out by mixing with stirring two starting compounds in the presence of a base such as sodium hydride, lithium tert-butoxide, etc., in a solvent such as anhydrous dimethylformamide. This step is carried out at a temperature of from 0 to 45° C. for 0.5 to 20 hours.

Step 2 is a step of reacting the compound (V) obtained in Step 1 with the compound (VI) to give the compound (VII). This reaction is carried out in the same manner as in Step 1. In this step, the protecting group R for carboxyl group in the compound (VI) may be the same ones as that in the compound (IV), but preferably different ones. For example, when one of the protecting groups is one to be decomposed with acid-base such as tert-butyl group, then the other should be one to be decomposed by hydrogenolysis such as benzyl group.

The compound (VII) thus obtained can be used as a starting compound in Step 3. Step 3 is carried out by removing the protecting group R for carboxyl group binding to B in the compound (VII) to give the compound (II') wherein W is a hydroxy group, and then if necessary, followed by converting it into a halogen atom, etc.

The acid-base decomposition, which is one of the methods for removing a protecting group R for carboxyl group, is carried out by contacting the above compound (VII) with an acid or a base at −30 to 100° C., preferably at a temperature of from 0° C. to room temperature in a solvent. The acid includes, for example, trifluoroacetic acid, hydrochloric acid, hydrobromic acid, sulfuric acid, acetic acid, etc., and the base includes, for example, sodium hydroxide, potassium hydroxide, etc. The solvent may be water, ethanol, methylene chloride, ethyl acetate, tetrahydrofuran, benzene, toluene, or a mixture of these solvents.

The removal of a protecting group R for carboxyl group by hydrogenolysis is preferably carried out by treating the compound (VII) with a hydrogen gas in the presence of a catalyst in a solvent. The catalyst includes, for example, platinum, palladium, Raney-nickel, etc., and the solvent may be ethyl acetate, ethanol, etc. This hydrogenolysis is carried out at a temperature of about 60° C. or below, usually at room temperature.

When the compound (II') wherein W is a hydroxy group is obtained by the removal of the protecting group for carboxyl group, then this hydroxy group is easily converted into another active group or a halogen atom, if necessary.

The compound (II') thus obtained is used as a starting compound in Step 4.

Step 4 is a step of combining the compound (II') and the compound (VIII) via an amide-bond to give the present compound (I-d). That is, this Step is carried out by a conventional method for peptide production. For example, Step 4 is carried out by mixing with stirring the compound (II') and the compound (VIII) in the presence or absence of a base such as triethylamine in a solvent such as methylene chloride or dimethylformamide or without a solvent. When W of the compound (II') is a hydroxyl group, this Step 4 is preferably carried out in the presence of a condensing agent such as 1-ethyl-3-(3-dimethylaminopropyl)carbodiimide, N,N'-dicyclohexylcarbodiimide, 1,1'-carbonyldiimidazole, N,N'-disuccinimidyl carbonate, etc. When W is a hydroxy group, this step may be carried out by reacting the compound (II') with ethyl chloroformate in the presence of a tertiary amine such as triethylamine, N-methylmorpholine, preferably N-methylmorpholine, and then further reacting the resultant with the compound (VIII).

Most of the compounds (VIII) are known compounds, and a compound (VIII) which is not known may be prepared by the method disclosed in Example 6 or 7 as described below or a modified method thereof.

The present compound (I-d) (OH-compound) thus obtained is a novel compound, and can be used as a direct starting compound in the preparation of the present compound (I-b) (ketone compound) which is useful as an elastase inhibitor. Step 5 is a step of oxidizing the hydroxy group of the compound (I-d), and then if necessary removing the protecting group for carboxyl group by a method as explained above. The oxidation reaction of this step is carried out by treating the compound (I-d) with an oxidizing agent in a solvent such as methylene chloride, dimethylformamide, tetrahydrofuran, ethyl acetate, toluene, etc.

The oxidizing agent includes a Dess-Martin reagent, which is a iodobenzene derivative. Besides, oxidation with phosphorus pentoxide in the presence of dimethylsulfoxide, oxidation with 1-ethyl-3-(3-dimethylaminopropyl) carbodiimide-$Cl_2CHCOOH$ in the presence of dimethylsulfoxide, and oxidation with a combination of oxalyl chloride and triethylamine (Swern oxidation) are also applicable.

Throughout all of the steps, when a free amino group or carboxyl group exists in the D-moiety, it is preferable to protect these groups with a conventional protecting group, if necessary, and then to remove said protecting group at an appropriate step.

When the present compound thus obtained is an ester compound, it can be converted into a carboxylic acid compound, or when the present compound is a carboxylic acid compound, then it can be converted into an ester compound, or can be converted into a salt thereof. In addition, when the present compound is in the form of various isomers, then these isomers can be separated by a conventional method.

BEST MODE FOR CARRYING OUT THE INVENTION

The present invention will be illustrated in more detail by Examples.

In Examples described below, the following abbreviations having the following meanings are occasionally used.

| | |
|---|---|
| t-Bu: | tert-butyl group |
| Bn: | benzyl group |
| LSIMS: | Liquid secondary ion mass spectrometry |
| $^1$H-NMR: | Proton nuclear magnetic resonance |
| APCIMS (or APCI-MS): | Atmospheric pressure chemical ionization mass spectrometry |
| IR: | Infrared spectrophotometry |

EXAMPLE 1

Preparation of Compound (VII) (Steps 1 and 2)

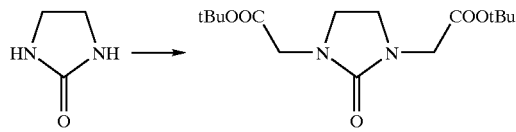

To anhydrous dimethylformamide (10 ml) containing 2-oxo-imidazolidine (0.30 g) and tert-butyl bromoacetate (1.50 g) are added lithium tert-butoxide (0.60 g) under ice-cooling, and the mixture is stirred at the same temperature for 30 minutes, and then stirred at room temperature for one hour. The reaction solution is poured into ice, and the precipitated crystals are washed with water and air-dried. Crude crystals thus obtained are recrystallized from ethyl acetate to give the desired 1,3-bis(tert-butoxycarbonylmethyl)-2-oxoimidazolidine (0.86 g) as white crystals.

M.p. 100–102° C.

LSIMS (m/z): 315 [(M+H)$^+$]

$^1$H-NMR (300 MHz, CDCl$_3$, δ): 1.46 (18H, s), 3.54 (4H, s), 3.89 (4H, s)

EXAMPLE 2

Preparation of Compound (VII) (Steps 1 and 2)
Step 1: Preparation of Compound (V)

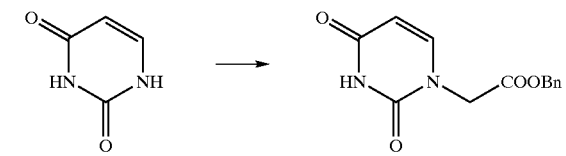

To anhydrous dimethylformamide solution (10 ml) containing 2,4-dioxopyrimidine (1.0 g) are added benzyl bromoacetate (2.5 g) and potassium carbonate (2.5 g), and the mixture is stirred at room temperature for 15 hours. The reaction solution is poured into water, and the mixture is extracted with ethyl acetate. The extract is washed with a saturated brine, and dried over anhydrous magnesium sulfate. The solvent is removed by evaporation under reduced pressure, and the precipitated crystals are washed with diethyl ether to give the desired 1-benzyloxycarbonylmethyl-2,4-dioxopyrimidine (1.4 g) as colorless crystals.

M.p. 192–194° C.

LSIMS (m/z): 261 [(M+H)+]

$^1$H-NMR (300 MHz, $d_6$-DMSO, 6): 4.59 (2H, s), 5.20 (2H, s), 5.62 (1H, d), 7.37 (5H, m), 7.65 (1H, d), 11.4 (1H, s)

Step 2: Preparation of Compound (VII)

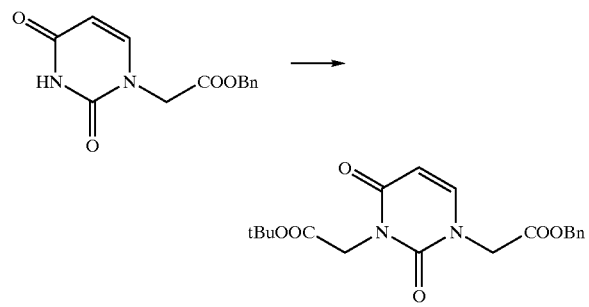

To anhydrous dimethylformamide (10 ml) containing the compound (1.0 g) obtained in the above step is gradually added sodium hydride (purity; 60%, 0.18 g) under ice-cooling, and the mixture is stirred under ice-cooling for 15 minutes. To the mixture is added tert-butyl bromoacetate (0.9 g), and the mixture is stirred at room temperature for one hour. Saturated aqueous ammonia chloride solution is added to the reaction mixture, and the mixture is extracted with ethyl acetate. The extract is washed with a saturated brine, dried over anhydrous magnesium sulfate, and the solvent is removed by evaporation under reduced pressure. The residue is purified by silica gel column chromatography [solvent; n-hexane:ethyl acetate (2:1)] to give the desired 1-benzyloxycarbonylmethyl-3-tert-butoxycarbonylmethyl-2,4-dioxopyrimidine (1.2 g) as colorless oil.

LSIMS (m/z): 375 [(M+H)+]

$^1$H-NMR (300 MHz, CDCl$_3$, 6): 1.46 (9H, s), 4.51 (2H, s), 4.58 (2H, s), 5.21 (2H, s), 5.81 (1H, d), 7.10 (1H, d), 7.36 (5H, m)

EXAMPLE 3

Preparation of Compound (II) (Step 3)

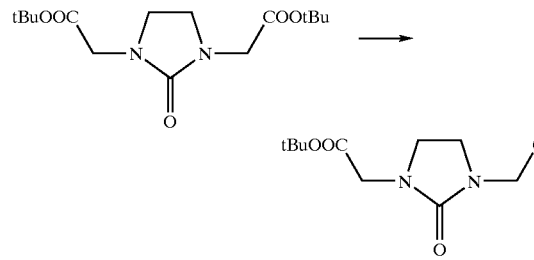

To a mixture of ethanol and water in equal volume (20 ml) containing 1,3-bis(tert-butoxycarbonylmethyl)-2-oxoimidazolidine (1.14 g) obtained in Example 1 is added potassium hydroxide (0.22 g), and the mixture is stirred at 70° C. for 5 hours. Ethanol is removed by evaporation under reduced pressure, and to the residue is added an aqueous saturated sodium hydrogen carbonate solution. The aqueous layer is washed with ethyl acetate, and acidified with a 10% hydrochloric acid, and extracted with ethyl acetate. The extract is dried over magnesium sulfate, and the solvent is removed by evaporation under reduced pressure. The precipitated crystals are recrystallized from ethyl acetate to give the desired 2-[(3-tert-butoxy-carbonylmethyl)-2-oxo-1-imidazolidinyl]acetic acid (0.30 g) as colorless crystals.

M.p. 112–113° C.

LSIMS (m/z): 259 [(M+H)+]

$^1$H-NMR (300 MHz, CDCl$_3$, δ): 1.46 (9H, s), 3.53 (4H, s), 3.89 (2H, s), 4.01 (21H, s), 7.11 (1H, br s)

EXAMPLE 4

Preparation of Compound (II) (Step 3)

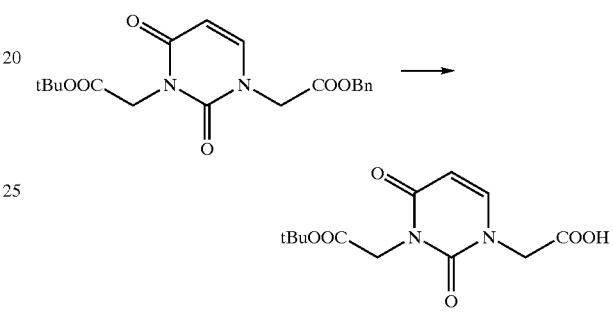

To ethyl acetate (20 ml) containing 1-benzyloxycarbonylmethyl-3-(tert-butoxycarbonylmethyl)-2,4-dioxopyrimidine (1.2 g) obtained in Example 2 is added a 20% palladium hydroxide (50 mg), and the mixture is stirred at room temperature under hydrogen atmosphere for one hour. The catalyst is removed by filtration, and the filtrate is concentrated under reduced pressure to give the desired 2-(3-tert-butoxycarbonylmethyl-2,4-dioxo-1-pyrimidinyl)acetic acid (0.7 g) as colorless powder.

$^1$H-NMR (300 MHz, CDCl$_3$, o): 1.46 (9H, s), 4.51 (2H, s), 4.59 (2H, s), 5.86 (1H, d), 7.17 (1H, d)

EXAMPLE 5

Preparation of Compound (II) (Step 3)

Compounds (VII) obtained in a similar manner as in Example 1 or Example 2 are treated in a similar manner as in Example 3 or Example 4 to give the compounds (II) as listed in Table 5 as described below.

TABLE 5

| Compound | Compound (II) | Physicochemical properties |
|---|---|---|
| II-4 | ![structure with t-BuOCO and COOH on piperazinedione] | LSIMS (m/z): 287 ([M + H]+) $^1$H-NMR (300 MHz, CDCl$_3$, δ): 1.47(9H, s), 3.71(4H, br s), 4.15(2H, br s), 4.22(2H, br s). |

TABLE 5-continued

| Compound | Compound (II) | Physicochemical properties |
|---|---|---|
| II-5 | t-BuOCO-[2,5-dioxopiperazine]-CH2COOH | LSIMS (m/z): 287 ([M + H]+) $^1$H-NMR (300 MHz, CDCl$_3$, δ): 1.41(9H, s), 3.32(1H, br s), 4.06(8H, m). |
| II-6 | t-BuOCO-[piperazine]-COOH | APCIMS (m/z): 259 ([M + H]+) $^1$H-NMR (300 MHz, CDCl$_3$, δ): 1.46(9H, s), 2.90(4H, br s), 3.18(2H, s), 3.32(4H, br s), 3.51(2H, s). |
| II-7 | t-BuOCO-[hydantoin]-COOH | LSIMS (m/z): 273 ([M + H]+) |
| II-9 | t-BuOCO-[methyl triazinedione]-COOH | LSIMS (m/z): 300 ([M + H]+) $^1$H-NMR (300 MHz, d$_6$-DMSO, δ): 1.42(9H, s), 2.17(3H, s), 4.48(2H, s), 4.60(2H, s), 13.28(1H, br s). |
| II-13 | t-BuOCO-[hydantoin isomer]-COOH | LSIMS (m/z): 273 ([M + H]+) |
| II-15 | t-BuOCO-[methyluracil]-COOH | LSIMS (m/z): 299 ([M + H]+) $^1$H-NMR (300 MHz, CDCl$_3$, δ): 1.48(9H, s), 1.96(3H, d), 4.49(2H, s), 4.61(2H, s), 6.98(1H, d). |
| II-16 | t-BuOCO-[uracil]-COOH | LSIMS (m/z): 285 ([M + H]+) $^1$H-NMR (300 MHz, CDCl$_3$ + CD$_3$OD, δ): 1.49(9H, s), 4.42(2H, s), 4.67(2H, s), 5.83(1H, d), 7.31(1H, d). |

TABLE 5-continued

| Compound | Compound (II) | Physicochemical properties |
|---|---|---|
| II-17 | t-BuOCO-[5,5-dimethylhydantoin]-COOH | LSIMS (m/z): 301 ([M + H]+) |
| II-19 | t-BuOCO-[dimethylhydantoin isomer]-COOH | LSIMS (m/z): 301 ([M + H]+) |
| II-20 | t-BuOCO-[dihydrouracil]-COOH | LSIMS (m/z): 287 ([M + H]+) |
| II-22 | t-BuOCO-[triazinone]-COOH | LSIMS (m/z): 286 ([M + H]+) |

EXAMPLE 6

Preparation of Compound (VIII)

(1) Preparation of the Benzylamino Compound (Benzylamination)

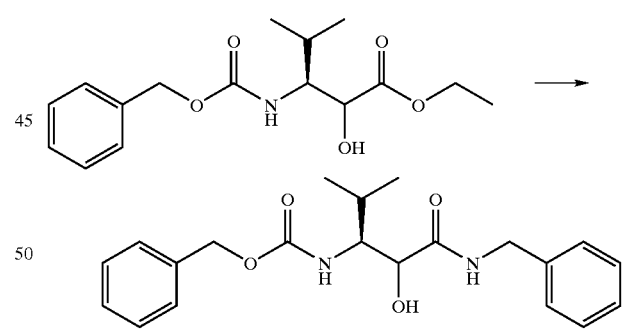

A suspension containing lithium aluminum hydride (1.2 g) and tetrahydrofuran (200 ml) is stirred under reflux for 1.5 hour. The reaction solution is cooled to room temperature, and thereto is added dropwise benzylamine (17.3 g). Then, to the mixture is added dropwise tetrahydrofuran (150 ml) containing (3S)-3-benzyloxycarbonylamino-2-hydroxy-4-methylbutyric acid ethyl ester (10 g), and the mixture is stirred at room temperature for 12 hours. Water is carefully added to the reaction solution, and the mixture is extracted with ethyl acetate. The extract is dried over magnesium sulfate, and the solvent is removed by evaporation under reduced pressure. The residue is purified by silica gel column chromatography [solvent; n-hexane:ethyl acetate (1:1)] to give the desired (1S)-3-benzylamino-1-benzyloxycarbonylamino-1-isopropyl-2-hydroxy-3-oxopropane (9.2 g) as colorless oil.

LSIMS (m/z): 371 [(M+H)$^+$]

$^1$H-NMR (300 MHz, CDCl$_3$, 5): 0.96 (3H, d), 1.02 (3H, d), 2.23 (1H, m), 3.47 (1H, br t), 4.23–4.55 (4H, m), 5.01 (2H, s), 5.19 (1H, m), 5.59 (1H, m), 7.06–7.44 (10H, m)

(2) Preparation of the Starting OH Compound (Removal of Protecting Group for Amino Group)

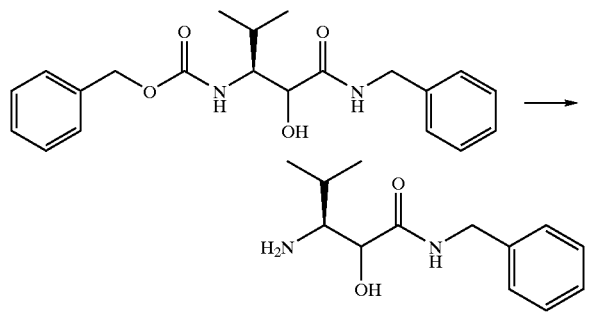

To ethanol (200 ml) containing the compound (9.2 g) obtained in the above step is added a catalytic amount of 20% palladium hydroxide, and the mixture is subjected to hydrogenolysis at room temperature. The catalyst is removed by filtration, and the filtrate is concentrated under reduced pressure to give the desired (1S)-1-amino-3-benzylamino-1-isopropyl-2-hydroxy-3-oxopropane (5.9 g) as colorless oil. This product is subjected to the subsequent reaction without further purification.

(3) Preparation of Compound (III) Having an Amino Group Protected (Amidation)

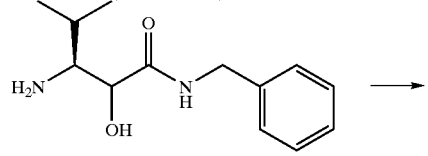

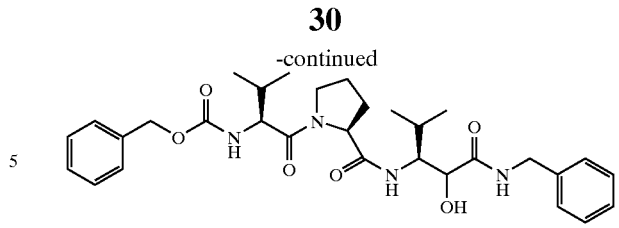

To methylene chloride (200 ml) containing the compound (5.9 g) obtained in the above step are added N-(benzyloxycarbonyl)-L-valyl-L-proline (9.7 g) and 1-ethyl-3-(3-dimethylaminopropyl)carbodiimide hydrochloride (5.3 g), and the mixture is stirred at room temperature for 12 hours, and concentrated under reduced pressure at room temperature. To the residue is added ethyl acetate, and the mixture is washed successively with 1 mol/liter hydrochloric acid, water, a saturated aqueous sodium hydrogen carbonate solution, and a saturated brine, and dried over anhydrous magnesium sulfate. The solvent is removed by evaporation under reduced pressure, and the residue is purified by silica gel column chromatography [solvent; chloroform-methanol (100:1)] to give the desired N-benzyloxycarbonyl-L-valyl-N-[(1S)-3-benzylamino-2-hydroxy-1-isopropyl-3-oxopropyl]-prolinamide (7.5 g) as colorless oil.

LSIMS (m/z): 567 [(M+H)$^+$]

$^1$H-NMR (300 MHz, CDCl$_3$, 8): 0.79–1.06 (12H, m), 1.77–2.35 (5H, m), 3.56 (1H, m), 3.73 (1H, m), 4.23–4.45 (4H, m), 5.06 (1H, d), 5.11 (1H, d), 5.48 (1H, br t), 7.17–7.42 (10H, m)

(4) Preparation of Compound (VIII) (Removal of a Protecting Group for Amino Group)

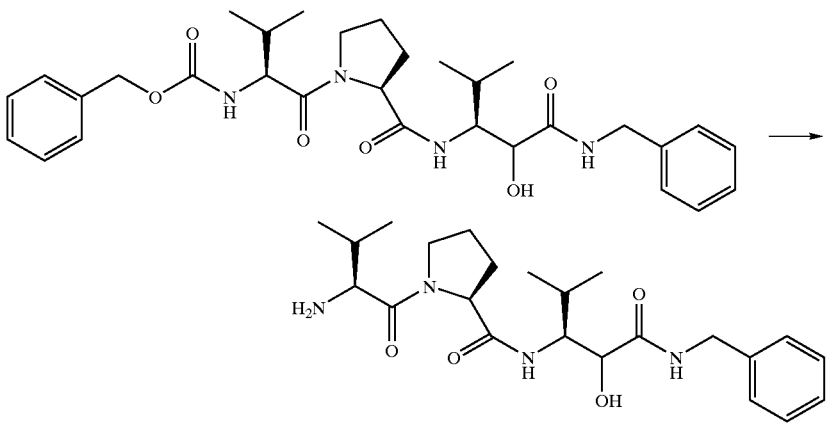

To a solution of the compound (9.2 g) obtained in the above step in ethanol (200 ml) is added a catalytic amount of 2% palladium hydroxide, and the mixture is stirred at room temperature under hydrogen current for one hour. The catalyst is removed by filtration, and the filtrate is concentrated under reduced pressure to give the desired L-valyl-N-[(1S)-(3-benzylamino-1-isopropyl-2-hydroxy-3-oxopropyl)-L-prolinamide (5.9 g) as colorless oil. This product is used as a starting compound in Example 10 without further purification.

EXAMPLE 7

Preparation of Compound (VIII)

(1) Preparation of the Starting Oxazolidine Derivative (Cyclization)

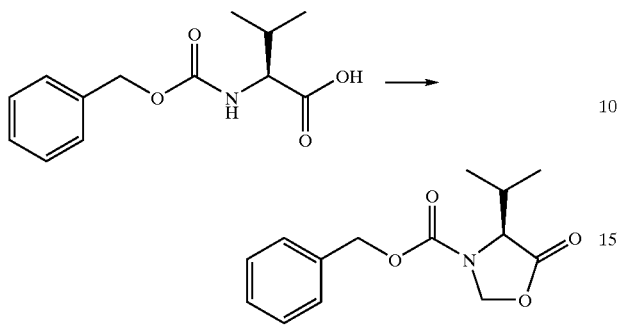

To a solution of N-benzyloxycarbonyl-L-valine (25.1 g, 0.1 mol) in toluene (500 ml) are added paraformaldehyde (4.0 g) and p-toluene-sulfonic acid monohydrate (1.0 g), and the mixture is refluxed for 30 minutes, during which the generated water is removed with a Dean-Stark apparatus. The reaction solution is washed successively with a 5% aqueous sodium hydrogen carbonate solution and a saturated brine, dried over magnesium sulfate, and the solvent is removed by evaporation under reduced pressure. The residue is recrystallized from toluene to give (4S)-4-isopropyl-5-oxo-1,3-oxazolidine-3-carboxylic acid benzyl ester (25.0 g, yield: 95%).

M.p. 54–55° C.

$[\alpha]_D^{24}$+98.2° (c=1.0, chloroform)

IR (KBr) cm$^{-1}$: 1786, 1691

$^1$H NMR (300 MHz, CDCl$_3$): δ 7.32–7.41 (5H, m), 5.15–5.60 (4H, m), 4.23 (1H, brs), 2.35 (1H, m), 1.08 (3H, d, J=6.78 Hz), 1.01 (3H, d, J=6.78 Hz)

APCI-MS: 264 (MH$^+$)

(2) Preparation of 5-Trifluoromethyloxazolidine Derivative (Trifluoromethylation)

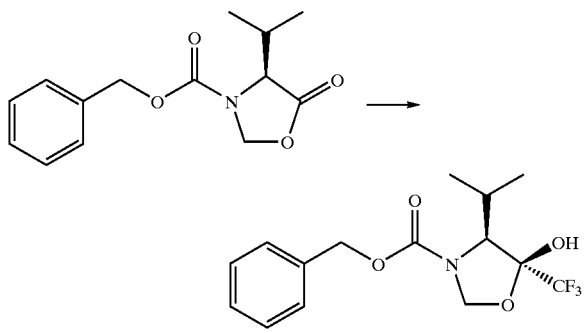

(4S)-4-Isopropyl-5-oxo-1,3-oxazolidine-3-carboxylic acid benzyl ester (5 g, 0.019 mol) obtained in the above is dissolved in tetrahydrofuran (15 ml), and thereto is added cesium fluoride (0.58 g, 0.0038 mol), and then further added slowly trimethyl(trifluoromethyl)silane (3.5 ml, 0.024 mol), and the mixture is stirred at room temperature for 30 minutes.

Subsequently, methanol (15 ml) is added to the above tetrahydrofuran solution, and the mixture is stirred for 5 minutes. The reaction mixture is concentrated under reduced pressure, and the residue is purified by silica gel column chromatography [eluent; n-hexane-ethyl acetate (15:1→10:1)], and further recrystallized from diisopropyl ether to give (4S,5S)-5-hydroxy-4-isopropyl-5-trifluoromethyl-1,3-oxazolidine-3-carboxylic acid benzyl ester (5.83 g, yield: 92%).

M.p. 73–74° C.

$[\alpha]_D^{24}$+48.2 (c=1.0, chloroform)

$^1$H NMR (300 MHz, CDCl$_3$): δ 7.34–7.40 (5H, m), 5.42 (1H, brs), 5.20 (1H, d, J=12.3 Hz), 5.15 (1H, d, J=12.3 Hz), 4.84 (1H, d, 4.92 Hz), 4.22 (1H, brs), 3.63 (1H, brs), 2.17–2.26 (1H, m), 1.05 (3H, d, J=5.67 Hz), 1.00 (3H, d, J=6.75 Hz)

APCI-MS: 334 (MH$^+$)

(3) Preparation of 5-Trifluoromethyl Derivative (Ring Opening)

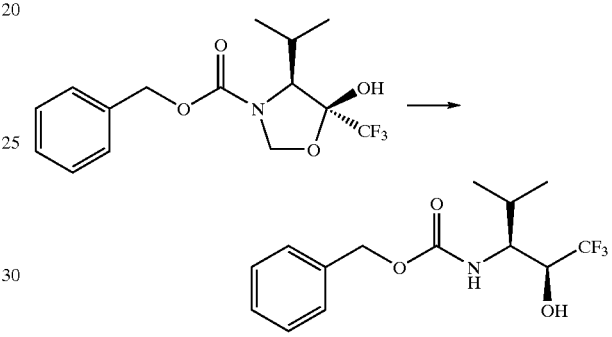

A solution of the ester (5.0 g, 0.015 mol) obtained in the above in t-butyl methyl ether (20 ml) is added dropwise to a solution of zinc chloride (2.0 g, 0.015 mol) and sodium borohydride (1.1 g, 0.029 mol) in t-butyl methyl ether (80 ml), and the mixture is stirred at room temperature for 15 hours. To the reaction solution is added a saturated aqueous ammonium chloride solution (80 ml), and the mixture is extracted with ethyl acetate (50 ml). The extract is washed with as saturated brine, and the organic layer is dried over magnesium sulfate. The solvent is removed by evaporation under reduced pressure, and methanol (25 ml), water (25 ml) and potassium carbonate (3.1 g) are added to the residue, and the mixture is stirred for one hour. The reaction solvent is removed by evaporation under reduced pressure, and water (50 ml) is added to the residue. The mixture is extracted three times with ethyl acetate (50 ml). The extract is washed with a saturated brine, and the organic layer is dried over magnesium sulfate, and the solvent is removed by evaporation under reduced pressure. The precipitated crystals are collected by filtration, and washed with hexane to give N-[(1S,2S)-3,3,3-trifluoro-2-hydroxy-1-(isopropyl)propyl] carbamic acid benzyl ester (3.0 g, yield: 87%).

M.p. 103–104° C.

$[\alpha]_D^{24}$-22.3 (c=1.0, chloroform)

$^1$H NMR (CDCl$_3$): δ 7.26–7.45 (5H, m), 5.14 (1H, d, J=12.1 Hz), 5.10 (1H, d, J=12.1 Hz), 4.84 (1H, d, J=9.0 Hz), 3.99–4.15 (1H, m), 3.81 (2H, m), 1.90–2.07 (1H, m), 1.01 (3H, d, J=6.6 Hz), 0.96 (3H, d, J=6.6 Hz)

APCI-MS: 306 (MH$^+$)

(4) Preparation of the Staring OH Compound (Removal of Protecting Group for Amino Group)

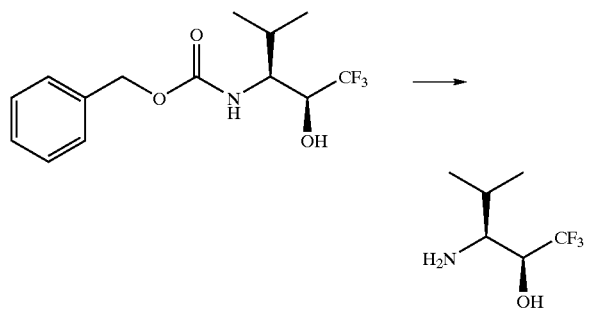

N-[(1S,2S)-3,3,3-Trifluoro-2-hydroxy-1-(isopropyl) propyl]-carbamic acid benzyl ester (740 g, 2.42 mol) obtained in a similar manner as in the above is dissolved in ethyl acetate (1500 ml), and thereto is added 20% palladium hydroxide (30 g), and the mixture is stirred at room temperature under hydrogen atmosphere for 7 hours. The catalyst is removed by filtration, and the filtrate is concentrated under reduced pressure to give (2S,3S)-3-amino-1,1,1-trifluoro-4-methyl-2-pentanol (420 g, yield: quantitative) as oil.

$^1$H NMR (CDCl$_3$): δ 3.95–4.02 (1H, m), 2.56–2.63 (1H, m), 1.77–1.92 (1H, m), 1.01 (3H, d, J=6.6 Hz), 0.99 (3H, d, J=6.6 Hz)

APCI-MS: 172 (MH$^+$)

(5) Preparation of Compound (VIII) (Amidation/Removal of Protecting Group for Amino Group)

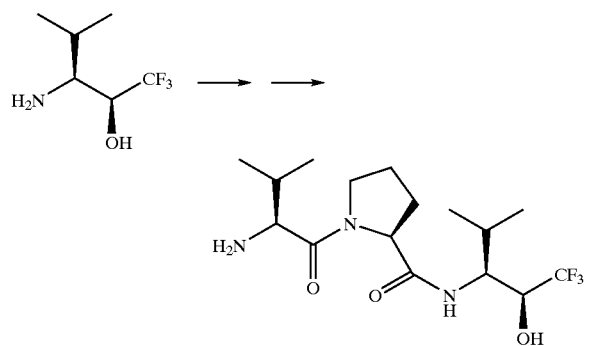

(2S,3S)-3-Amino-1,1,1-trifluoro-4-methyl-2-pentanol obtained in the above and N-(benzyloxycarbonyl)-L-valyl-L-proline are reacted in a similar manner as in Example 6 (3), and the resulting product is treated in a similar manner as in Example 6 (4) to remove a benzyloxycarbonyl group, which is a protecting group for amino group, to give the desired L-valyl-N-[(1S,2S)-3,3,3-trifluoro-1-isopropyl-2-hydroxypropyl)-L-prolinamide hydrochloride.

EXAMPLE 8

Preparation of Compound (I-d-1) (Step 4)

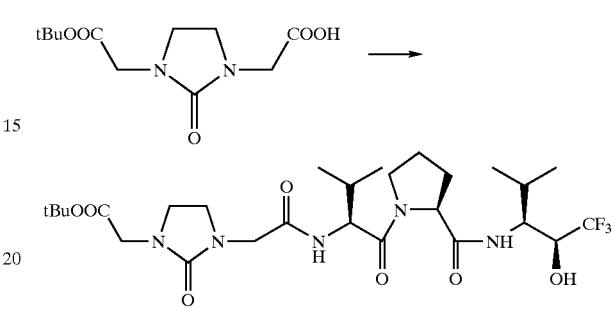

To methylene chloride (1000 ml) containing 2-[(3-tert-butoxy-carbonylmethyl-2-oxo-1-imidazolidinyl)]acetic acid (33 g) obtained in Example 3 and L-valyl-N-[(1S,2S)-(3,3,3-trifluoro-1-isopropyl-2-hydroxypropyl)]-L-prolinamide hydrochloride (46.4 g) obtained in Example 7(5) are added 1-ethyl-3-(3-dimethylaminopropyl)carbodiimide hydrochloride (41.4 g) and triethylamine (38.5 g), and the mixture is stirred at room temperature for 12 hours, and concentrated under reduced pressure at room temperature. To the residue is added ethyl acetate, and the mixture is washed successively with 1 mol/liter hydrochloric acid, water, a saturated aqueous sodium hydrogen carbonate solution, and a saturated brine, and dried over anhydrous magnesium sulfate. The solvent is removed by evaporation under reduced pressure, and the residue is purified by silica gel column chromatography [solvent; chloroform-methanol (100:3)] to give the desired 2-(3-tert-butoxycarbonylmethyl-2-oxo-1-imidazolidinyl)acetyl-L-valyl-N-[(1S,2S)-(3,3,3-trifluoro-1-isopropyl-2-hydroxypropyl)]-L-prolinamide (79.5 g) as colorless oil.

APCIMS (m/z): 608 [(M+H)$^+$]

EXAMPLE 9

Preparation of Compound (I-d-2) (Step 4)

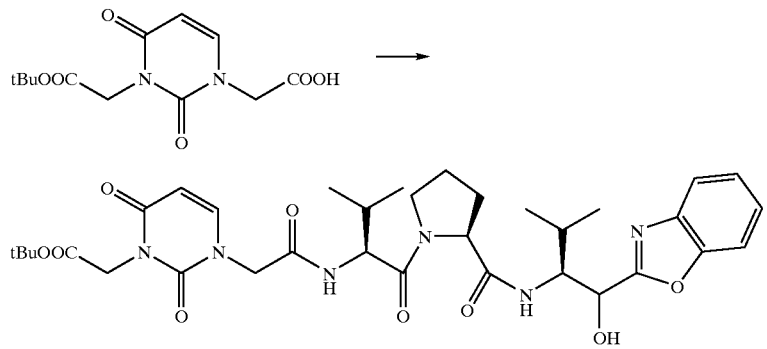

To pyridine (20 ml) containing L-valyl-N-[(1S)-2-(2-benzoxazolyl)-1-isopropyl-2-hydroxyethyl]-L-prolinamide (1.0 g) are added 2-(3-tert-butoxycarbonylmethyl-2,4-dioxo-1-pyrimidinyl)acetic acid (0.7 g) obtained in Example 4 and 1-ethyl-3-dimethylaminopropyl)carbodiimide hydrochloride (0.6 g), and the mixture is stirred at room temperature for 15 hours. The reaction solution is poured into water, and the mixture is extracted with ethyl acetate. The extract is washed successively with 1 mol/liter hydrochloric acid, a saturated aqueous sodium hydrogen carbonate solution, and a saturated brine, and dried over anhydrous magnesium sulfate. The solvent is removed by evaporation under reduced pressure to give the desired 2-(3-tert-butoxycarbonylmethyl-2,4-dioxo-1-pyrimidinyl)acetyl-L-valyl-N-[(1S)-2-(2-benzoxazolyl)-1-isopropyl-2-hydroxyethyl]-L-prolinamide (1.5 g) as powders.

LSIMS (m/z): 683 [(M+H)$^+$]

EXAMPLE 10

Preparation of Compound (I-d) (Step 4)

The compounds (VIII) obtained in Example 6 or Example 7 are treated in a similar manner as in Example 8 or Example 9 to give the compounds (I-d) as listed in Table 6 as described below.

TABLE 6

Compound I-d

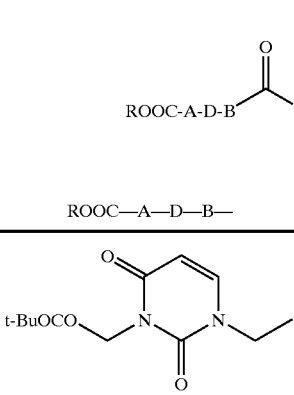

| No. | ROOC—A—D—B— | R$^5$ | Physicochemical properties |
|---|---|---|---|
| Id3 | 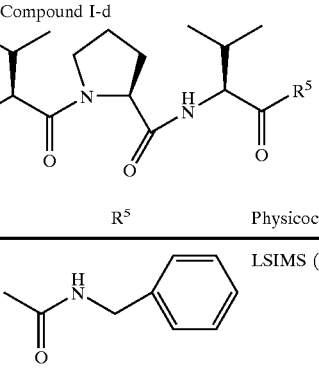 | 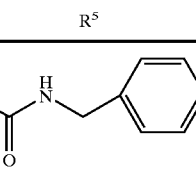 | LSIMS (m/z): 699 ([M + H]$^+$) |
| Id4 | 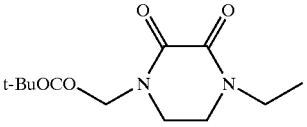 | 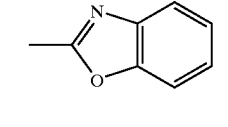 | LSIMS (m/z): 685 ([M + H]$^+$) |
| Id5 | 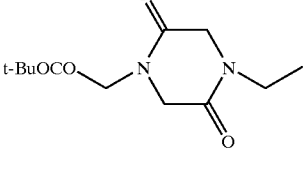 | 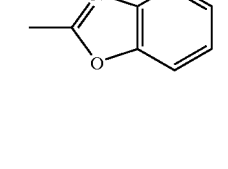 | LSIMS (m/z): 685 ([M + H]$^+$) |
| Id6 | 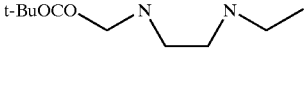 | 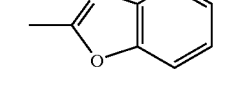 | APCIMS (m/z): 657 ([M + H]$^+$) |
| Id7 | 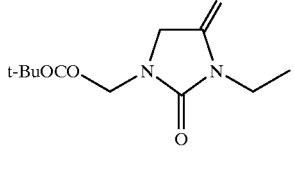 | CF$_3$ | APCIMS (m/z): 622 ([M + H]$^+$)<br>$^1$H-NMR (300 MHz, CDCl$_3$, δ):<br>0.92–1.00(12H, m), 1.47(9H, s), 1.97–2.24(5H, m), 3.62–3.85 (3H, m), 4.06–4.10(3H, m), 4.20–4.38(2H, m), 4.47–4.53 (1H, m), 4.60–4.67(1H, m), 4.86 and 5.02(1H, each d), 6.91 and 7.15(1H, each d), 7.34(1H, d). |
| Id9 | 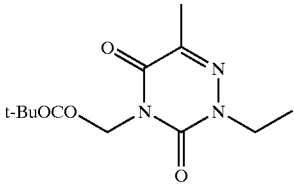 | 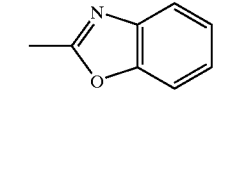 | APCIMS (m/z): 698 ([M + H]$^+$)<br>$^1$H-NMR (300 MHz, CDCl$_3$, δ):<br>0.82–1.08(12H, m), 1.47(9H, s), 1.74–2.52(8H, m), 3.48–3.73 (2H, m), 3.95–4.78(7H, m), 5.01–5.33(1H, m), 6.96–7.89 (6H, m). |

TABLE 6-continued

Compound I-d: ROOC-A-D-B-NH-CH(iPr)-C(O)-N(pyrrolidine)-C(O)-NH-CH(iPr)-C(O)-R⁵

| No. | ROOC—A—D—B— | R⁵ | Physicochemical properties |
|---|---|---|---|
| Id11 | t-BuOCO-CH₂-(uracil-N1), N3-ethyl | —COOCH₃ | LSIMS (m/z): 624 ([M + H]⁺)<br>¹H-NMR (300 MHz, CDCl₃, δ): 0.86–1.04(12H, m), 1.45(9H, s), 1.87–2.06(5H, m), 3.61–3.76 (2H, m), 3.79(3H, s), 4.08–4.69 (8H, m), 5.82(1H, d), 7.03–7.18 (2H, m), 7.21(1H, d). |
| Id12 | t-BuOCO-CH₂-(2,3-dioxopiperazin-N1), N4-ethyl | —C(O)NHCH₂Ph (benzyl) | LSIMS (m/z): 701 ([M + H]⁺) |
| Id13 | t-BuOCO-CH₂-(2,4-dioxoimidazolidin-N3), N1-ethyl | 2-benzoxazolyl | APCIMS (m/z): 671 ([M + H]⁺)<br>¹H-NMR (300 MHz, CDCl₃, δ): 0.82–1.01(12H, m), 1.45(9H, s), 1.58–2.05(8H, m), 3.51–4.34(9H, m), 4.54–4.67(2H, m), 5.00–5.33(1H, m), 7.15–7.84(7H, m). |
| Id14 | t-BuOCO-CH₂-(2,4-dioxoimidazolidin-N1), N3-ethyl | 2-benzoxazolyl | APCIMS (m/z): 671 ([M + H]⁺) |
| Id15 | t-BuOCO-CH₂-(5-methyluracil-N1), N3-ethyl | 2-benzoxazolyl | LSIMS (m/z): 697 ([M + H]⁺) |
| Id16 | t-BuOCO-CH₂-(uracil-N1), N3-ethyl | 2-benzoxazolyl | LSIMS (m/z): 683 ([M + H]⁺) |
| Id17 | t-BuOCO-CH₂-(5,5-dimethyl-2,4-dioxoimidazolidin-N3), N1-ethyl | 2-benzoxazolyl | APCIMS (m/z): 699 ([M + H]⁺)<br>¹H-NMR (300 MHz, CDCl₃, δ): 0.84–0.99(12H, m), 1.42(6H, s), 1.46(9H, s), 1.58–2.20(6H, m), 3.65–3.80(2H, m), 3.91 (2H, s), 4.17–4.82(6H, m), 5.08–5.32(1H, m), 7.28–7.74 (6H, m). |
| Id18 | t-BuOCO-CH₂-(2-oxoimidazolidin-N1), N3-ethyl | 2-benzoxazolyl | LSIMS (m/z): 657 ([M + H]⁺) |

TABLE 6-continued

Compound I-d

ROOC-A-D-B—NH—CH(iPr)—C(O)—N(pyrrolidine)—C(O)—NH—CH(iPr)—C(O)—R⁵

| No. | ROOC—A—D—B— | R⁵ | Physicochemical properties |
|---|---|---|---|
| Id19 | t-BuOCO-CH₂-(5,5-dimethyl-3-ethyl-2,4-dioxoimidazolidin-1-yl) | 2-benzoxazolyl | LSIMS (m/z): 699 ([M + H]⁺)<br>¹H-NMR (300 MHz, CDCl₃, δ): 0.81–1.03(12H, m), 1.44(15H, s), 1.66–2.53(6H, m), 3.40–3.70(4H, m), 4.04–4.22(4H, m), 4.50–4.60(2H, m), 5.13–5.28(2H, m), 7.29–7.66(6H, m). |
| Id20 | t-BuOCO-CH₂-(3-ethyl-2,4-dioxotetrahydropyrimidin-1-yl) | 2-benzoxazolyl | APCIMS (m/z): 685 ([M + H]⁺) |
| Id21 | t-BuOCO-CH₂-(4-ethyl-2,3-dioxopiperazin-1-yl) | COOCH₃ | LSIMS (m/z): 626 ([M + H]⁺) |
| Id22 | t-BuOCO-CH₂-(2-ethyl-3,5-dioxo-1,2,4-triazin-4-yl) | 2-benzoxazolyl | LSIMS (m/z): 684 ([M + H]⁺) |
| Id23 | t-BuOCO-CH₂-(3-ethyl-2,4-dioxopyrimidin-1-yl) | CF₃ | APCIMS (m/z): 634 ([M + H]⁺) |
| Id24 | t-BuOCO-CH₂-(4-ethyl-2,3-dioxopiperazin-1-yl) | CF₃ | LSIMS (m/z): 636 ([M + H]⁺)<br>¹H-NMR (300 MHz, CDCl₃, δ): 0.92–1.03(12H, m), 1.45(9H, s), 2.00–2.23(6H, m), 3.62–3.84(2H, m), 4.04–4.87(7H, m), 5.82(1H, d), 7.24(1H, d), 7.49–7.52(1H, m). |
| Id25 | t-BuOCO-CH₂-(4-ethylpiperazin-1-yl) | C(O)NHCH₂Ph | LSIMS (m/z): 673 ([M + H]⁺) |

EXAMPLE 11

Preparation of Compound (I-b-1) (Step 5)

Step 5-1: Preparation of the Ketone Compound (Oxidation)

Step 5-2: Preparation of Compound (I-b) (Removal of Protecting Group for Carboxyl Group)

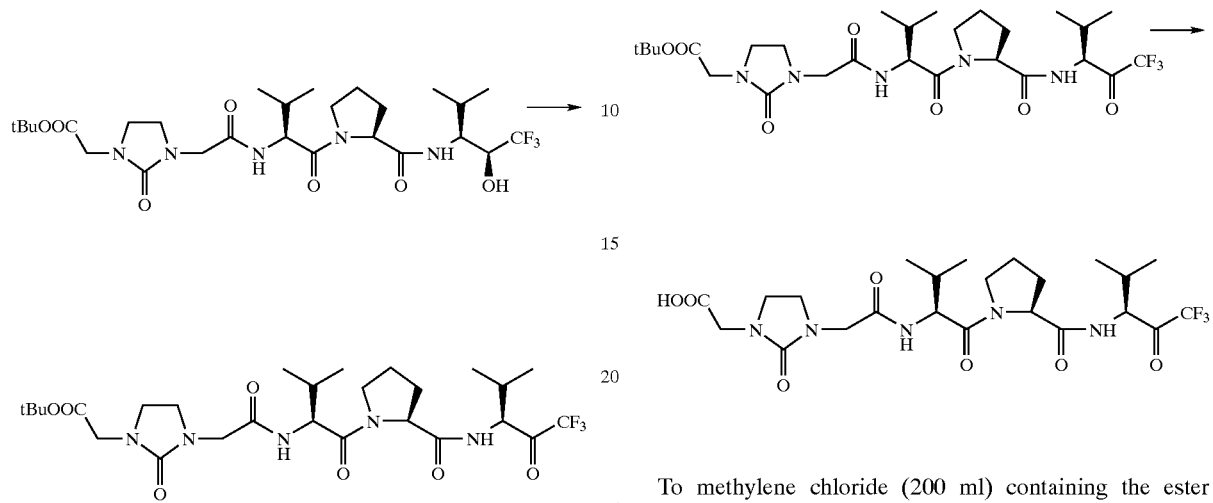

To methylene chloride (1000 ml) containing 2-(3-tert-butoxy-carbonylmethyl-2-oxo-1-imidazolidinyl)acetyl-L-valyl-N-[(1S,2S)-3,3,3-trifluoro-1-isopropyl-2-hydroxypropyl]-L-prolinamide (79.5 g) obtained in Example 8 is added a Dess-Martin reagent (112.3 g), and the mixture is stirred at room temperature for one hour, and the mixture is concentrated under reduced pressure. To the residue is added ethyl acetate, and the mixture is washed successively with a saturated aqueous sodium thiosulfate solution, water, a saturated aqueous sodium hydrogen carbonate, and a saturated brine, and dried over anhydrous magnesium sulfate. The solvent is removed by evaporation under reduced pressure, and the residue is purified by silica gel column chromatography [solvent; chloroform-methanol (100:3)] to give the desired 2-(3-tert-butoxycarbonylmethyl-2-oxo-1-imidazolidinyl)acetyl-L-valyl-N-[(1 S)-(3,3,3-trifluoro-1-isopropyl-2-oxopropyl)]-L-prolinamide (67.2 g) as colorless oil.

APCIMS (m/z): 606 [(M+H)$^+$]

$^1$H-NMR (300 MHz, CDCl$_3$, a): 0.83–1.02 (12H, m), 1.47 (9H, s), 1.89–2.32 (6H, m), 3.48–4.06 (10H, m), 4.58 (114, dd), 4.64 (1H, dd), 4.84 (1H, dd), 7.35 (1H, d), 7.72 (1H, d)

To methylene chloride (200 ml) containing the ester compound (34.9 g) obtained in the above Step (5-1) is added trifluoroacetic acid (200 ml) at room temperature, and the mixture is stirred at room temperature for one hour, and concentrated under reduced pressure. To the residue is added diisopropyl ether, and the precipitated crystals are collected by filtration, and crystallized from ethyl acetate. The crystals are further recrystallized from ethyl acetate-methyl ethyl ketone to give the desired 2-(3-carboxymethyl-2-oxo-1-imidazolidinyl)acetyl-L-valyl-N-[(1S)-3,3,3-trifluoro-1-isopropyl-2-oxopropyl]-L-prolinamide (17.3 g) as colorless crystals. According to high performance liquid chromatography, it is confirmed that the purity of the product is 98.71%, and that 0.78% of the isomer is contained therein.

M.p. 177–178° C.

[α]$_D^{20}$ –63.0° (c=1.0, chloroform)

APCIMS (m/z): 550 [(M+H)$^+$]

$^1$H-NMR (300 MHz, CDCl$_3$, 3): 0.85–1.02 (12H, m), 1.90–2.31 (6H, m), 3.51 (4H, m), 3.68 (1H, m), 3.81–4.13 (5H, m), 4.58 (2H, m), 4.92 (1H, dd), 7.45 (2H, m)

EXAMPLE 12

Preparation of Compound (I-b-2) (Step 5)

Step 5-1: Preparation of the Ketone Compound (Oxidation)

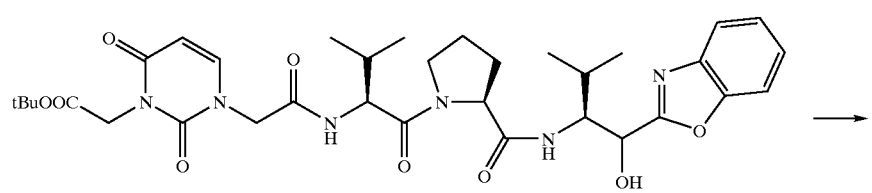

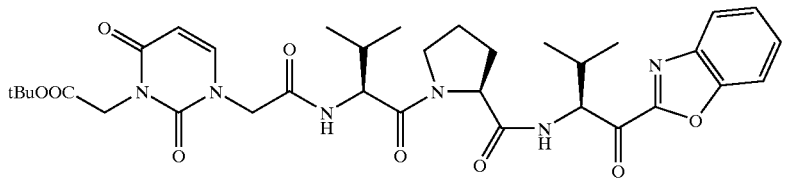

To methylene chloride (30 ml) containing 2-(3-tert-butoxy-carbonylmethyl-2,4-dioxo-1-pyrimidinyl)acetyl-L-valyl-N-[(1S)-2-(2-benzoxazolyl)-1-isopropyl-2-hydroxyethyl]-L-prolinamide (1.5 g) obtained in Example 9 are added t-butyl alcohol (0.16 g) and a Dess-Martin reagent (1.9 g), and the mixture is stirred at room temperature for one hour. The reaction solution is poured into a saturated aqueous sodium thiosulfate solution, and the mixture is extracted with ethyl acetate. The extract is washed successively with a saturated aqueous sodium thiosulfate solution, a saturated aqueous sodium hydrogen carbonate solution, and a saturated brine, and dried over anhydrous magnesium sulfate. The solvent is removed by evaporation under reduced pressure to give the desired 2-(3-tert-butoxycarbonylmethyl-2,4-dioxo-1-pyrimidinyl)acetyl-L-valyl-N-[(1S)-2-(2-benzoxazolyl)-1-isopropyl-2-oxoethyl]-L-prolinamide (1.2 g) as powders.

LSIMS (m/z): 681 [(M+H)+]

$^1$H-NMR (300 MHz, CDCl$_3$, δ): 0.90–1.09 (12H, m), 1.44 (9H, s), 1.90–2.30 (5H, m), 2.50 (1H, m), 3.67 (1H, m), 3.78 (1H, m), 4.26 (1H, d), 4.54–4.75 (5H, m), 5.69 (1H, dd), 5.83 (1H, d), 7.42–7.57 (4H, m), 7.66 (1H, d), 7.91 (1H, d)

Step 5-2: Preparation of Compound (I-b) (Removal of Protecting Group for Carboxyl Group)

To a solution of the ester compound (1.2 g) obtained in the above Step (5-1) in methylene chloride (30 ml) is added trifluoroacetic acid (15 ml), and the mixture is stirred at room temperature for one hour. The reaction solution is concentrated under reduced pressure, and to the residue is added water, and the mixture is extracted with ethyl acetate. The extract is washed with water, and dried over anhydrous magnesium sulfate. The solvent is concentrated under reduced pressure, and ether is added to the residue for pulverization. The resultant is recrystallized from dichloroethane to give the desired 2-(3-carboxymethyl-2,4-dioxo-1-pyrimidinyl)acetyl-L-valyl-N-[(1S)-2-(2-benzoxazolyl)-1-isopropyl-2-oxoethyl]-L-prolinamide (1.2 g) as powders. According to high performance liquid chromatography, it is confirmed that the purity of the product is 92%, and that 7.1% of the isomer is contained therein.

M.p. 135–140° C.

LSIMS (m/z): 625 [(M+H)+]

$^1$H-NMR (300 MHz, d$_6$-DMSO, δ): 0.85–1.05 (12H, m), 1.70–2.05 (5H, m), 2.38 (1H, m), 3.55 (1H, m), 3.64 (1H, m), 4.32 (1H, dd), 4.40–4.55 (5H, m), 5.28 (1H, dd), 5.75 (1H, d), 7.55 (1H, dd), 7.64 (2H, m), 7.90 (1H, d), 8.01 (1H, d), 8.45 (2H, m), 12.9 (1H, s)

EXAMPLE 13

Preparation of Compound (I-b) (Step 5)

The compounds (I-b) as listed in Table 7 are obtained in a similar manner as in Example 11 or Example 12.

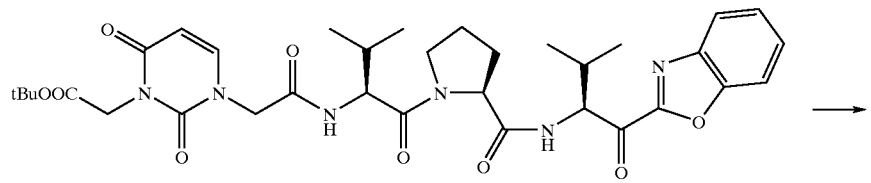

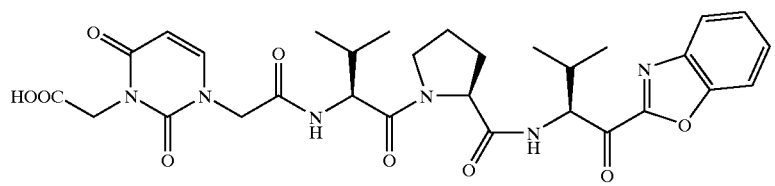

TABLE 7

Compound I-b

ROOC-A-D-B-[C(=O)-NH-Val-Pro-Val-NH-C(=O)-R⁵ structure]

| No. | ROOC—A—D—B— | R⁵ | Physicochemical properties |
|---|---|---|---|
| Ib3 | HOOC-CH₂-[N-ethyl uracil-N-] | -NH-C(=O)-CH₂-NH-C(=O)-CH₃ (benzyl acetamide) | LSIMS (m/z): 641 ([M + H]⁺)<br>¹H-NMR (300 MHz, CDCl₃, δ): 0.75–1.06(12H, m), 1.88–2.50(6H, m), 3.65(1H, m), 3.78(1H, m), 4.35–4.69(7H, m), 4.94(1H, d), 5.82(1H, d), 7.15(1H, d), 7.18–7.40(5H, m). |
| Ib3' | t-Bu ester of the above compound | The same as above | LSIMS (m/z): 697 ([M + H]⁺)<br>¹H-NMR (300 MHz, CDCl₃, δ): 0.83(3H, d), 0.88–1.07(9H, m), 1.45(9H, s), 1.86–2.28 (5H, m), 2.38(1H, m), 3.65 (1H, m), 3.76(1H, m), 4.22 (1H, d), 4.47(2H, d), 4.54–4.72(5H, m), 5.29(1H, dd), 5.81(1H, d), 7.18–7.41(8H, |
| Ib4 | HOOC-CH₂-[N-ethyl dioxopiperazine] | benzoxazole-2-yl | LSIMS (m/z): 627 ([M + H]⁺)<br>¹H-NMR (300 MHz, CDCl₃, δ): 0.82–1.13(12H, m), 1.90–2.73(6H, m), 3.56–3.90(6H, m), 4.13–4.36(4H, m), 4.54–4.69(2H, m), 5.64(1H, dd), 7.39(1H, br d), 7.47(1H, t), 7.55(1H, t), 7.66(1H, d), 7.74(1H, br d), 7.91(1H, d). |
| Ib4' | t-Bu ester of the above compound | The same as above | LSIMS (m/z): 683 ([M + H]⁺) |
| Ib5 | HOOC-CH₂-[N-ethyl dioxopiperazine isomer] | benzoxazole-2-yl | LSIMS (m/z): 627 ([M + H]⁺)<br>¹H-NMR (300 MHz, CDCl₃, δ): 0.86–1.11(12H, m), 1.91–2.25 (5H, m), 2.51(1H, m), 3.19(1H, br s), 3.69(1H, m), 3.83(1H, m), 4.00–4.31(8H, m), 4.55–4.69(2H, m), 5.65(1H, dd), 7.36–7.59(3H, m), 7.66(2H, d), 7.91(1H, d). |
| Ib5' | t-Bu ester of the above compound | The same as above | LSIMS (m/z): 683 ([M + H]⁺)<br>¹H-NMR (300 MHz, CDCl₃, δ): 0.82–1.16(12H, m), 1.48(9H, s), 1.90–2.29(5H, m), 2.50(1H, m), 3.67(1H, m), 3.78(1H, m), 3.87–4.42(8H, m), 4.65(1H, br t), 4.73(1H, br t), 5.69(1H, dd), 7.48(1H, br t), 7.54(1H, br t), 7.66(1H, br d), 7.91(1H, d). |
| ☆ Ib6 | HOOC-CH₂-[N-ethyl piperazine] | benzoxazole-2-yl | LSIMS (m/z): 599 ([M + H]⁺)<br>¹H-NMR (300 MHz, d₆-DMSO, δ): 0.84–1.00(12H, m), 1.71–2.06 (5H, m), 2.39(1H, m), 3.29–4.03 (14H, m), 4.37(1H, dd), 4.51 (1H, m), 5.28(1H, dd), 7.56(1H, dd), 7.66(1H, dd), 7.91(1H, d), 8.02(1H, d), 8.47(1H, m), 8.69 (1H, m). |

TABLE 7-continued

Compound I-b

ROOC-A-D-B-[structure with Val-Pro-Val backbone]-R⁵

| No. | ROOC—A—D—B— | R⁵ | Physicochemical properties |
|---|---|---|---|
| Ib6' | t-Bu ester of the above compound | The same as above | APCIMS (m/z): 655 ([M + H]⁺) ¹H-NMR (300 MHz, CDCl₃, δ): 0.92–1.14(12H, m), 1.47(9H, s), 1.60–2.73(14H, m), 3.00–3.15(4H, m), 3.68(1H, m), 3.83 (1H, m), 4.57–4.76(2H, m), 5.58 (1H, m), 7.21–7.93(6H, m). |
| Ib7 | HOOC—CH₂—(ethyl-hydantoin) | CF₃ | APCIMS (m/z): 564 ([M + H]⁺) ¹H-NMR (300 MHz, d₆-DMSO, δ): 0.77–0.94(12H, m), 1.69–2.23(6H, m), 3.53–3.72(2H, m), 4.04–4.12 (6H, m), 4.30–4.63(4H, m), 8.40 (1H, d), 8.61(1H, d), 13.02(1H, br s). |
| Ib7' | t-Bu ester of the above compound | The same as above | APCIMS (m/z): 620 ([M + H]⁺) ¹H-NMR (300 MHz, CDCl₃, δ): 0.86–1.08(12H, m), 1.48(9H, s), 1.70–2.46(6H, m), 3.60–3.80(2H, m), 4.07(2H, s), 4.10(2H, s), 4.19–4.34(2H, m), 4.62–4.70(2H, m), 4.86 and 4.93(1H, each dd), 6.89 and 7.04(1H, each d), 7.58 and 7.81(1H, each d). |
| Ib8 | HOOC—CH₂—(N-piperazinyl-propanoyl) | 2-benzoxazolyl | LSIMS (m/z): 655 ([M + H]⁺) ¹H-NMR (300 MHz, d₆-DMSO, δ): 0.83–1.00(12H, m), 1.71–2.09(5H, m), 2.39(1H, m), 3.34–3.56(14H, m), 3.69(1H, m), 4.33(1H, dd), 4.50(1H, m), 5.29(1H, m), 7.55 (1H, dd), 7.65(1H, dd), 7.90(1H, d), 8.02(1H, d), 8.26(1H, m), 8.43 (1H, m). |
| Ib8' | t-Bu ester of the above compound | The same as above | LSIMS (m/z): 711 ([M + H]⁺) |
| Ib9 | HOOC—CH₂—(methyl-ethyl-triazinedione) | 2-benzoxazolyl | APCIMS (m/z): 640 ([M + H]⁺) ¹H-NMR (300 MHz, d₆-DMSO, δ): 0.85–1.01(12H, m), 1.71–2.06(5H, m), 2.15(3H, s), 2.36–2.42(1H, m), 3.48–3.66(2H, m), 4.31(1H, dd), 4.47(2H, s), 4.52(1H, dd), 4.60(2H, s), 5.28(1H, dd), 7.53–7.68(2H, m), 7.96(2H, dd), 8.46 (2H, m) |
| Ib9' | t-Bu ester of the above compound | The same as above | APCIMS (m/z): 696 ([M + H]⁺) ¹H-NMR (300 MHz, CDCl₃, δ): 0.92–1.14(12H, m), 1.48(9H, s), 1.98–2.23(5H, m), 2.26(3H, s), 2.44–2.55(1H, m), 3.64–3.79(2H, m), 4.51–4.77(6H, m), 5.66(1H, dd), 6.90(1H, d), 7.43–7.67(4H, m), 7.91(1H, d) |

TABLE 7-continued

Compound I-b

ROOC-A-D-B-[structure with valine-proline-valine tripeptide backbone, terminal R⁵]

| No. | ROOC—A—D—B— | R⁵ | Physicochemical properties |
|---|---|---|---|
| Ib10 | [structure: HOOC-CH2-piperazinone with N-propionyl] | [2-methylbenzoxazole] | LSIMS (m/z): 641 ([M + H]⁺)<br>¹H-NMR (300 MHz, d₆-DMSO, δ): 0.85–1.00(12H, m), 1.71–2.06(5H, m), 2.39(1H, m), 3.33–4.16(12H, m), 4.32(1H, m), 4.50(1H, m), 5.31(1H, m), 7.55(1H, dd), 7.65(1H, dd), 7.90(1H, d), 8.02(1H, d), 8.29 (1H, m), 8.43(1H, d) |
| Ib10' | t-Bu ester of the above compound | The same as above | LSIMS (m/z): 697 ([M + H]⁺)<br>¹H-NMR (300 MHz, CDCl₃, δ): 0.92–1.13(12H, m), 1.47(9H, s), 1.85–2.55(6H, m), 3.38–4.31(12H, m), 4.55–4.79(2H, m), 5.59(1H, m), 7.43–7.92 (6H, m) |
| Ib11 | [structure: HOOC-CH2-N-ethyluracil] | COOCH₃ | APCIMS (m/z): 566 ([M + H]⁺)<br>¹H-NMR (300 MHz, d₆-DMSO, δ): 0.81–0.92(12H, m), 1.69–2.27(7H, m), 3.77(3H, s), 4.31–4.61(7H, m), 5.74(1H, d), 7.66(1H, d), 8.38–8.48(2H, m). |
| Ib11' | t-Bu ester of the above compound | The same as above | APCIMS (m/z): 622 ([M + H]⁺)<br>¹H-NMR (300 MHz, CDCl₃, δ): 0.79–1.06(12H, m), 1.46(9H, s), 1.93–2.32(5H, m), 3.59–3.75(2H, m), 3.89(3H, s), 4.24–4.56(2H, m), 4.58(4H, s), 5.08(1H, dd), 5.82(1H, d), 6.72(1H, d), 7.20(1H, d). |
| Ib12 | [structure: HOOC-CH2-N-ethyl-2,3-dioxopiperazine] | [benzylaminocarbonylmethyl] | LSIMS (m/z): 643 ([M + H]⁺)<br>¹H-NMR (300 MHz, d₆-DMSO, δ): 0.73–1.00(12H, m), 1.67–2.30(6H, m), 4.00–4.20(5H, m), 4.23–4.42(4H, m), 4.49 (1H, m), 4.95 and 5.01(1H, each dd), 8.16(1H, d), 8.32 (1H, d), 9.24(1H, t). |
| Ib12' | t-Bu ester of the above compound | The same as above | LSIMS (m/z): 699 ([M + H]⁺) |
| Ib13 | [structure: HOOC-CH2-N-ethylimidazolidine-2,4-dione] | [2-methylbenzoxazole] | APCIMS (m/z): 613 ([M + H]⁺)<br>¹H-NMR (300 MHz, d₆-DMSO, δ): 0.83–1.01(12H, m), 1.72–2.09(5H, m), 2.36–2.42(1H, m), 3.51–3.74(2H, m), 4.05–4.14(6H, m), 4.34(1H, t), 4.52(1H, dd), 5.29(1H, dd), 7.53–7.69(2H, m), 7.96(2H, dd), 8.37(1H, d), 8.44(1H, d). |
| Ib13' | t-Bu ester of the above compound | The same as above | APCIMS (m/z): 669 ([M + H]⁺) |

TABLE 7-continued

Compound I-b

ROOC-A-D-B-[structure with Val-Pro-Val-R⁵ peptide backbone]

| No. | ROOC—A—D—B— | R⁵ | Physicochemical properties |
|---|---|---|---|
| Ib14 | HOOC-CH₂-N(hydantoin with N-ethyl) | 2-methylbenzoxazole | APCIMS (m/z): 613 ([M + H]⁺)<br>¹H-NMR (300 MHz, d₆-DMSO, δ): 0.84–1.01(12H, m), 1.72–2.04(5H, m), 2.35–2.40(1H, m), 3.49–3.69(2H, m), 4.04–4.12(6H, m), 4.31(1H, t), 4.52(1H, dd), 5.26–5.30(1H, m), 7.53–7.68(2H, m), 7.96(2H, dd), 8.41(1H, d), 8.43(1H, d), 13.03(1H, br s) |
| Ib14' | t-Bu ester of the above compound | The same as above | APCIMS (m/z): 669 ([M + H]⁺)<br>¹H-NMR (300 MHz, CDCl₃, δ): 0.91–1.14(12H, m), 1.48(9H, s), 1.98–2.26(6H, m), 2.46–2.52(1H, m), 3.65–3.78(2H, m), 4.07(2H, s), 4.10(2H, s), 4.21–4.35(2H, m), 4.42–4.64(2H, m), 5.58–5.69(1H, m), 6.94(1H, d), 7.43–7.67(4H, m), 7.91(1H, d) |
| Ib15 | HOOC-CH₂-N(thymine-like with N-ethyl) | 2-methylbenzoxazole | LSIMS (m/z): 639 ([M + H]⁺)<br>¹H-NMR (300 MHz, d₆-DMSO, δ): 0.86–1.01(12H, m), 1.68–2.04(5H, m), 1.81(3H, s), 2.38(1H, m), 3.36–3.68(6H, m), 4.31(1H, dd), 4.50(1H, dd), 5.28(1H, dd), 7.53–7.68(3H, m), 7.90(1H, d), 8.02(1H, d), 8.45(2H, m) |
| Ib15' | t-Bu ester of the above compound | The same as above | APCIMS (m/z): 695 ([M + H]⁺)<br>¹H-NMR (300 MHz, CDCl₃, δ): 0.84–1.13(12H, m), 1.45(9H, s), 1.96(3H, s), 1.94–2.26(5H, m), 2.51(1H, m), 3.67(1H, m), 3.79(1H, m), 4.22(1H, d), 4.56–4.72(5H, m), 5.68(1H, m), 7.11(1H, s), 7.44–7.68(5H, m), 7.91(1H, d) |
| Ib16 | HOOC-CH₂-N(uracil with N-ethyl) | 2-methylbenzoxazole | LSIMS (m/z): 625 ([M + H]⁺)<br>¹H-NMR (300 MHz, d₆-DMSO, δ): 0.82–1.01(12H, m), 1.71–2.05(5H, m), 2.38(1H, m), 3.53(1H, m), 3.62(1H, m), 4.29(1H, dd), 4.41–4.52(5H, m), 5.27(1H, dd), 5.75(1H, d), 7.55(1H, ddd), 7.65(1H, ddd), 7.72(1H, d), 7.90(1H, d), 8.02(1H, d), 8.35(1H, d), 8.47(1H, d) |
| Ib16' | t-Bu ester of the above compound | The same as above | LSIMS (m/z): 681 ([M + H]⁺)<br>¹H-NMR (300 MHz, CDCl₃, δ): 0.92–1.13(12H, m), 1.48(9H, s), 1.87–2.32(5H, m), 2.48(1H, m), 3.62(1H, m), 3.76(1H, m), 4.38(2H, s), 4.60–4.77(4H, m), 5.63(1H, dd), 5.83(1H, d), 6.78(1H, d), 7.11(1H, d), 7.43–7.67(4H, m), 7.91(1H, d) |

TABLE 7-continued

Compound I-b

| No. | ROOC—A—D—B— | R⁵ | Physicochemical properties |
|---|---|---|---|
| Ib17 | HOOC-CH₂-(5,5-dimethyl-3-ethyl-2,4-dioxoimidazolidin-1-yl) | 2-benzoxazolyl | LSIMS (m/z): 641 ([M + H]⁺)<br>¹H-NMR (300 MHz, d₆-DMSO, δ): 0.84–1.01(12H, m), 1.31(6H, s), 1.71–2.07(5H, m), 2.34–2.42 (1H, m), 3.49–3.65(2H, m), 4.04–4.06(4H, m), 4.35(1H, dd), 4.52(1H, dd), 5.28(1H, dd), 7.53–7.68(2H, m), 7.96 (2H, dd), 8.36(1H, d), 8.45(1H, d), 12.83(1H, br d) |
| Ib17' | t-Bu ester of the above compound | The same as above | LSIMS (m/z): 697 ([M + H]⁺) |
| Ib18 | HOOC-CH₂-(3-ethyl-2-oxoimidazolidin-1-yl) | 2-benzoxazolyl | LSIMS (m/z): 599 ([M + H]⁺)<br>¹H-NMR (300 MHz, CDCl₃, δ): 0.82–1.13(12H, m), 1.88–2.28 (5H, m), 2.50(1H, m), 3.25–3.74 (5H, m), 3.82–4.12(5H, m), 4.54–4.71(2H, m), 5.65(1H, m), 7.35–7.59(4H, m), 7.66(1H, d), 7.91(1H, d) |
| Ib18' | t-Bu ester of the above compound | The same as above | LSIMS (m/z): 655 ([M + H]⁺) |
| Ib19 | HOOC-CH₂-(4,4-dimethyl-3-ethyl-2,5-dioxoimidazolidin-1-yl) | 2-benzoxazolyl | APCIMS (m/z): 641 ([M + H]⁺)<br>¹H-NMR (300 MHz, d₆-DMSO, δ): 0.83–1.01(12H, m), 1.29(6H, s), 1.72–2.02(4H, m), 2.33–2.44 (1H, m), 3.50–3.72(2H, m), 3.99(2H, s), 4.09(2H, s), 4.35 (1H, dd), 4.50(1H, dd), 5.27 (1H, dd), 7.53–7.68(2H, m), 7.96(2H, dd), 8.22(1H, d), 8.43 (1H, d), 13.12(1H, br s) |
| Ib19' | t-Bu ester of the above compound | The same as above | APCIMS (m/z): 697 ([M + H]⁺)<br>¹H-NMR (300 MHz, CDCl₃, δ): 0.92–1.08(12H, m), 1.46(15H, s), 1.90–2.18(4H, m), 2.28–2.34 (1H, m), 2.44–2.50(1H, m), 3.59–3.78(2H, m), 3.98(2H, s), 4.19(2H, s), 4.46–4.58(2H, m), 5.57(1H, dd), 6.82(1H, d), 7.43–7.67(4H, m), 7.91(1H, d) |
| Ib20 | HOOC-CH₂-(3-ethyl-2,4-dioxotetrahydropyrimidin-1-yl) | 2-benzoxazolyl | LSIMS (m/z): 627 ([M + H]⁺)<br>¹H-NMR (300 MHz, d₆-DMSO, δ): 0.82–1.00(12H, m), 1.70–2.04 (5H, m), 2.38(1H, m), 2.70(2H, t), 3.46(2H, t), 3.50(1H, m), 3.63 (1H, m), 4.07(2H, s), 4.25(2H, s), 4.29(1H, m), 4.51(1H, dd), 5.27 (1H, dd), 7.55(1H, dd), 7.65(1H, dd), 7.90(1H, d), 8.02(1H, d), 8.19(1H, d), 8.44(1H, d) |

TABLE 7-continued

Compound I-b

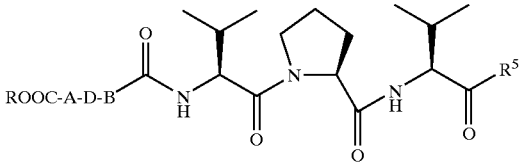

| No. | ROOC—A—D—B— | R⁵ | Physicochemical properties |
|---|---|---|---|
| Ib20' | t-Bu ester of the above compound | The same as above | APCIMS (m/z): 683 ([M + H]⁺) ¹H-NMR (300 MHz, CDCl₃, δ): 0.92–1.13(12H, m), 1.47(9H, s), 1.93–2.08(4H, m), 2.26(1H, m), 2.48(1H, m), 2.87(2H, t), 3.52 (2H, m), 3.61(1H, m), 3.72(1H, m), 4.09(2H, s), 4.46(1H, d), 4.58(1H, d), 4.66(2H, m), 5.61 (1H, dd), 6.61(1H, d), 7.44–7.67 (4H, m), 7.91(1H, d) |
| Ib21 | 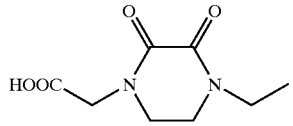 | COOCH₃ | LSIMS (m/z): 568 ([M + H]⁺) ¹H-NMR (300 MHz, CDCl₃, δ): 0.81–1.38(12H, m), 1.86–3.00 (7H, m), 3.53–3.95(9H, m), 4.03–4.35(4H, m), 4.47–4.69(2H, m), 5.02(1H, m) |
| Ib21' | t-Bu ester of the above compound | The same as above | LSIMS (m/z): 624 ([M + H]⁺) |
| Ib22 | 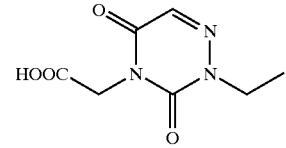 | 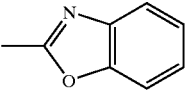 | APCIMS (m/z): 626 ([M + H]⁺) ¹H-NMR (300 MHz, CDCl₃, δ): 0.84–1.00(12H, m), 1.70–2.06 (5H, m), 2.38(1H, m), 3.53(1H, m), 3.61(1H, m), 4.31(1H, dd), 4.45(2H, s), 4.51(1H, dd), 4.64 (2H, s), 5.27(1H, dd), 7.55(1H, dd), 7.65(1H, dd), 7.71(1H, s), 7.90(1H, d), 8.02(1H, d), 8.45 (1H, d), 8.48(1H, d) |
| Ib22' | t-Bu ester of the above compound | The same as above | APCIMS (m/z): 682 ([M + H]⁺) ¹H-NMR (300 MHz, CDCl₃, δ): 0.92–1.14(12H, m), 1.48(9H, s), 1.90–2.30(5H, m), 2.49(1H, m), 3.64(1H, m), 3.72(1H, m), 4.60–4.75(6H, m), 5.64(1H, m), 7.44–7.57(2H, m), 7.47(1H, s), 7.66 (1H, d), 7.91(1H, d) |
| Ib23 | 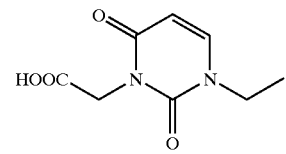 | CF₃ | APCIMS (m/z): 576 ([M + H]⁺) ¹H-NMR (300 MHz, d₆-DMSO, δ): 0.79–0.95(12H, m), 1.69–2.23 (8H, m), 3.53–3.72(2H, m), 4.24–4.64(6H, m), 5.75(1H, d), 7.66(1H, d), 8.46–8.63(2H, m), 12.94(1H, br s) |
| Ib23' | t-Bu ester of the above compound | The same as above | APCILSIMS (m/z): 632 ([M + H]⁺) ¹H-NMR (300 MHz, CDCl₃, δ): 0.86–1.08(12H, m), 1.46(9H, s), 1.91–2.35(6H, m), 3.62–3.82 (2H, m), 4.24(1H, dd), 4.58–4.71(5H, m), 4.86–4.95(1H, m), 5.83(1H, d), 7.25(1H, d), 7.38–7.72(2H, m) |
| Ib24 | 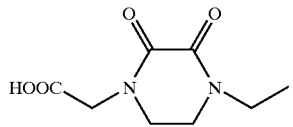 | CF₃ | LSIMS (m/z): 578 ([M + H]⁺) ¹H-NMR (300 MHz, d₆-DMSO, δ): 0.72–1.06(12H, m), 1.65–2.33 (6H, m), 3.50–3.78(6H, m), 3.98–4.18(5H, m), 4.30–4.65 (3H, m), 8.34(1H, t) |

TABLE 7-continued

Compound I-b

ROOC-A-D-B—[structure with peptide backbone]—R⁵

| No. | ROOC—A—D—B— | R⁵ | Physicochemical properties |
| --- | --- | --- | --- |
| Ib24' | t-Bu ester of the above compound | The same as above | LSIMS (m/z): 634 ([M + H]⁺) |
| ☆ Ib25 | HOOC—CH₂—N(piperazine)N—CH₂CH₃ | —CH₂—NH—C(=O)—CH₂—phenyl | LSIMS (m/z): 615 ([M + H]⁺)<br>¹H-NMR (300 MHz, d₆-DMSO, δ):<br>0.77–1.07(12H, m), 1.68–2.28<br>(5H, m), 3.33–3.77(10H, m),<br>3.83–4.17(4H, m), 4.23–4.38<br>(4H, m), 4.98(1H, m), 7.10–7.50<br>(5H, m), 8.19(1H, d), 9.26(1H, dd) |
| Ib25' | t-Bu ester of the above compound | The same as above | LSIMS (m/z): 671 ([M + H]⁺) |

☆2 hydrochloride

EXAMPLE A

Method for Preparing Liquid Preparation

TABLE 8

| Formulation | |
| --- | --- |
| Compound I-b-1 | 500 mg |
| Sorbitol | 5 g |
| Sodium hydroxide | q.s. |
| Distilled water for injection | q.s. |
| | 100 ml |

Compound (I-b-1) and sorbitol are dissolved in a portion of distilled water for injection, and thereto is added the rest of the distilled water. The pH value of the solution is adjusted to pH 4.0, and the solution thus obtained is filtered through a membrane filter (0.22 μm) to give a liquid preparation for injection.

EXAMPLE B

Preparation of Lyophilized Preparation

TABLE 9

| Formulation | |
| --- | --- |
| Compound I-b-1 | 500 mg |
| Mannitol | 5 g |
| Sodium hydroxide | q.s. |
| Distilled water for injection | q.s. |
| | 100 ml |

Compound (I-b-1) and mannitol are dissolved in a portion of distilled water for injection, and thereto is added the rest of the distilled water for injection. The pH value of the solution is adjusted to pH 4.0, and the solution thus obtained is filtered through a membrane filter (0.22 μm), and the resultant is lyophilized to give a powder preparation for injection.

INDUSTRIAL APPLICABILITY

The present invention provides a novel compound. The present compound exhibits an excellent human neutrophilic elastase inhibitory activity, and is useful in the prophylaxis or treatment of various diseases, especially acute pulmonary diseases. In addition, the present invention also provides an intermediate for preparing the above compound.

What is claimed is:

1. A heterocyclic compound of the formula (I-a):

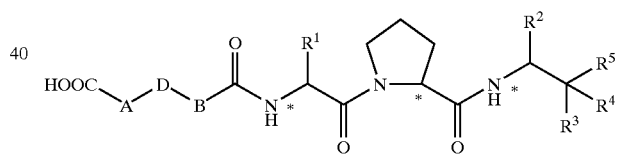

(I-a)

wherein * means that the carbon atom marked with * is an asymmetric carbon atom, A and B are the same or different and each is a lower alkylene group being optionally substituted by an oxo group, D is a heteromonocyclic or heterobicyclic group of the following formula:

wherein $D^1$ is a methylene group or an ethylene group, and these groups may optionally be substituted by an oxo group, Ring G is a 5- to 14-membered, saturated or unsaturated, heteromonocyclic or heterobicyclic group optionally having other heteroatoms selected from a nitrogen atom, an oxygen atom and/or a sulfur atom, and said heteromonocyclic or heterobicyclic group being optionally substituted by a substituent $T^1$ in which $T^1$ is the same or different 1 to 3 groups selected from (i) an oxo group, (ii) a substituted or unsubstituted lower alkyl group, (iii) a substituted or unsubstituted amino group, (iv) a substituted or unsubstituted carbamoyl group, (v) a carboxyl group or a lower alkoxycarbonyl group, (vi) a phenyl group being optionally substituted by a halogen atom, a lower alkoxy group or a, lower alkyl group, and (vii) a substituted or unsubstituted lower alkylcarbonyl group, $R^1$ and $R^2$ are the same or different and each is a lower alkyl group, $R^3$ and $R^4$ are different from each other, and each is a hydrogen atom or a hydroxy group, or both combine together to form an oxo group, $R^5$ is a group of the formula:

$$-\underset{X^1}{\overset{(C)_n}{\diagup}}\underset{X^2}{\overset{}{\diagdown}}-(CH_2)_m-Y^1$$

wherein $X^1$ and $X^2$ are a halogen atom, $Y^1$ is a hydrogen atom, a halogen atom, a lower alkoxycarbonyl group, a lower alkylaminocarbonyl group, an aralkylaminocarbonyl group, an aralkyloxycarbonyl group, a lower alkylcarbonyl group, or an aralkylcarbonyl group, or a group of the following formula:

$$-\overset{N}{\underset{U}{\diagdown}}Q$$

wherein U is an oxygen atom or a sulfur atom, Q is a vinylene group or an orthophenylene group being optionally substituted by $T^2$, $T^2$ is 1 to 3 groups selected from a halogen-substituted or unsubstituted lower alkyl group, a lower alkoxy group, a lower alkylsulfonyl group, a lower alkylcarbonyloxy group and an amino group being optionally substituted by a lower alkyl group, n is 0, 1 or 2, and m is an integer of 0 to 5, or its ester, or a salt thereof.

2. The heterocyclic compound according to claim 1, which is a compound of the following formula (I-b):

(I-b)

wherein A, B, D, $R^1$, $R^2$ and $R^5$ are as defined in claim 1, or its ester, or a salt thereof.

3. The heterocyclic compound according to claim 1, wherein the group of the formula: -A-D-B- is a group of the following formula:

$$-A-\overset{G'}{\underset{D^1}{N\diagup\diagdown N}}-B-$$

wherein A, B and $D^1$ are as defined in claim 1, Ring $G^1$ is a 5- to 9-membered, saturated or unsaturated heteromonocyclic group having optionally 1 to 3 of other heteroatom selected from a nitrogen atom, an oxygen atom and/or a sulfur atom, and said heteromonocyclic group may have 1 to 3 substitutents $T^1$ which are as defined in claim 1, or its ester, or a salt thereof.

4. The heterocyclic compound according to claim 1, wherein the group of the formula: -A-D-B- is a group of the following formula:

$$-A^1-\overset{D^2-D^3}{\underset{D^1}{N\diagup\diagdown N}}-B^1-$$

wherein $A^1$ is a methylene group or a group of the formula: —$CH_2CO$—, $B^1$ is a methylene group or a group of the formula: —$COCH_2$—, $D^2$ and $D^3$ are the same or different and each is a vinylene group optionally substituted by a lower alkyl group, or a methylene group optionally substituted by an oxo group or a lower alkyl group, $D^1$ is as defined in claim 1, provided that both $D^2$ and $D^3$ are not simultaneously a vinylene group optionally substituted by a lower alkyl group, or its ester, or a salt thereof.

5. The heterocyclic compound according to claim 4, which is a compound of the following formula (I-c):

(I-c)

wherein $D^1$ and $R^5$ are as defined in claim 1, and $A^1$, $B^1$, $D^2$ and $D^3$ are the same as defined in claim 4, or its ester, or a salt thereof.

6. The heterocyclic compound according to claim 5 selected from the group consisting of:

2-(3-carboxymethyl-2-oxo-1-imidazolidinyl)acetyl-L-valyl-N-[(1S)-3,3,3-trifluoro-1-isopropyl-2-oxopropyl]-L-prolinamide;

2-(3-carboxymethyl-2,4-dioxo-1-pyrimidinyl)-acetyl-L-valyl-N-[(1S)-2-(2-benzoxazolyl)-1-isopropyl-2-oxoethyl]-L-prolinamide;

2-(4-carboxymethyl-2,3-dioxo-1-piperazinyl)acetyl-L-valyl-N-[(1S)-2-(2-benzoxazolyl)-1-isopropyl-2-oxoethyl]-L-prolinamide;

2-(3-carboxymethyl-2,4-dioxo-1-pyrimidinyl)-acetyl-L-valyl-N-[(1S)-3-benzylamino-1-isopropyl-2,3-dioxopropyl]-L-prolinamide, 2-(4-carboxymethyl-2,5-dioxo-1-piperazinyl)acetyl-L-valyl-N-[(1S)-2-(2-benzoxazolyl)-1-isopropyl-2-oxoethyl]-L-prolinamide;

2-(3-carboxymethyl-2,5-dioxo-1-imidazolidinyl)-acetyl-L-valyl-N-[(1S)-3,3,3-trifluoro-1-isopropyl-2-oxopropyl]-L-prolinamide; and

[[4-(2-carboxyacetyl)-1-piperazinyl]malonyl]-L-valyl-N-[(1S)-2-(2-benzoxazolyl)-1-isopropyl-2-oxoethyl]-L-prolinamide or its ester, or a salt thereof.

7. A mixture comprising 90% or more of 2-(3-carboxymethyl-2-oxo-1-imidazolidinyl)acetyl-L-valyl-N-[(1S)-3,3,3-trifluoro-1-isopropyl-2-oxopropyl]-L-prolinamide, or a salt thereof, and the remaining % consisting substantially of a stereoisomer of 2-(3-carboxymethyl-2-oxo-1-imidazolidinyl)acetyl-L-valyl-N-[(1S)-3.3.3-trifluoro-1-isopropyl-2-oxopropyl]-L-prolinamide or a salt thereof.

8. A composition comprising a pharmaceutically acceptable carrier and a compound of the following formula (I-b):

(I-b)

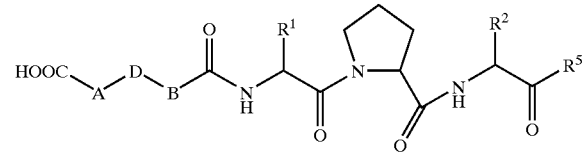

wherein A, B, D, $R^1$, $R^2$ and $R^5$ are as defined in claim 1, or a pharmaceutically acceptable salt thereof in an amount effective to inhibit human neutrophil elastase.

9. A pharmaceutical composition comprising a pharmaceutically acceptable carrier and a compound of the following formula (I-b):

(I-b)

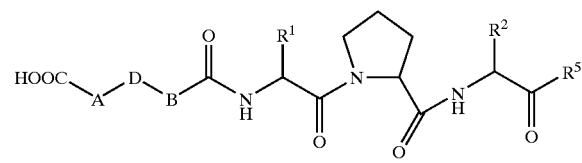

wherein A, B, D, $R^1$, $R^2$ and $R^5$ are as defined in claim 1, or a pharmaceutically acceptable salt thereof.

* * * * *